US010827929B2

(12) United States Patent
Ternes et al.

(10) Patent No.: US 10,827,929 B2
(45) Date of Patent: Nov. 10, 2020

(54) OBTAINING HIGH-RESOLUTION INFORMATION FROM AN IMPLANTABLE MEDICAL DEVICE

(71) Applicant: Cardiac Pacemakers, Inc., St. Paul, MN (US)

(72) Inventors: David J. Ternes, Roseville, MN (US); Zhe Shen, Arden Hills, MN (US); Stephen B. Ruble, Lino Lakes, MN (US); Pramodsingh H. Thakur, Woodbury, MN (US); Keith R. Maile, New Brighton, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 786 days.

(21) Appl. No.: 15/401,003

(22) Filed: Jan. 7, 2017

(65) Prior Publication Data

US 2017/0196458 A1 Jul. 13, 2017

Related U.S. Application Data

(60) Provisional application No. 62/276,383, filed on Jan. 8, 2016.

(51) Int. Cl.
*A61B 5/0402* (2006.01)
*G16H 40/67* (2018.01)
(Continued)

(52) U.S. Cl.
CPC .......... *A61B 5/0031* (2013.01); *A61B 5/0022* (2013.01); *A61B 5/0402* (2013.01);
(Continued)

(58) Field of Classification Search
CPC ... A61B 5/0031; A61B 5/0022; A61B 5/0402; A61B 5/0816; A61B 5/1118;
(Continued)

(56) References Cited

U.S. PATENT DOCUMENTS 4,172,459 A 10/1979 Hepp
4,552,154 A 11/1985 Hartlaub
(Continued)

FOREIGN PATENT DOCUMENTS

WO WO9965393 A1 12/1999
WO 2009114755 A2 9/2009
WO 2011034468 A1 3/2011

OTHER PUBLICATIONS

International Search Report and Written Opinion issued in PCT/US2017/020831, dated Jun. 16, 2017, 11 pages.
(Continued)

*Primary Examiner* — Navin Natnithithadha
(74) *Attorney, Agent, or Firm* — Faegre Drinker Biddle & Reath LLP

(57) ABSTRACT

Embodiments of the disclosure include systems and methods for obtaining high-resolution data from implantable medical devices (IMDs) by triggering a limited-time system behavior change. For example, embodiments include utilizing study prescriptions for batching data obtained by an IMD, communicating the batched data to an external device, and reconstructing the batched data at the external device. Study prescriptions refer to sets of instructions, conditions, protocols, and/or the like, that specify one or more of an information gathering scheme and a communication scheme, and may be configured, for example, to obtain information at a resolution sufficient for performing a certain analysis (e.g., associated with a diagnostic model), while managing the resulting impact to device longevity and/or performance.

19 Claims, 11 Drawing Sheets

(51) Int. Cl.
*G16H 10/20* (2018.01)
*G16H 20/40* (2018.01)
*A61B 5/00* (2006.01)
*A61B 5/08* (2006.01)
*A61B 7/02* (2006.01)
*A61B 5/11* (2006.01)
*A61N 1/372* (2006.01)

(52) U.S. Cl.
CPC .......... *A61B 5/0816* (2013.01); *A61B 5/1118* (2013.01); *A61B 5/4836* (2013.01); *A61B 5/686* (2013.01); *A61B 7/023* (2013.01); *A61N 1/37276* (2013.01); *G16H 10/20* (2018.01); *G16H 20/40* (2018.01); *G16H 40/67* (2018.01); *A61B 2560/0204* (2013.01); *A61B 2560/0209* (2013.01)

(58) Field of Classification Search
CPC ....... A61B 5/4836; A61B 5/686; A61B 7/023; A61B 2560/0204; A61B 2560/0209; G16H 20/40; G16H 40/67; G16H 10/20; A61N 1/37276
USPC ......................................................... 600/302
See application file for complete search history.

(56) References Cited

U.S. PATENT DOCUMENTS

| | | | |
|---|---|---|---|
| 5,127,404 A | 7/1992 | Wyborny et al. | |
| 5,251,621 A | 10/1993 | Collins | |
| 5,800,466 A | 9/1998 | Routh et al. | |
| 5,833,623 A | 11/1998 | Mann et al. | |
| 5,902,250 A | 5/1999 | Verrier et al. | |
| 5,904,708 A | 5/1999 | Goedeke | |
| 6,073,049 A | 6/2000 | Alt et al. | |
| 6,076,015 A | 6/2000 | Hartley et al. | |
| 6,132,384 A | 10/2000 | Christopherson et al. | |
| 6,190,324 B1 | 2/2001 | Kieval et al. | |
| 6,490,479 B2 | 12/2002 | Bock | |
| 6,804,558 B2 | 10/2004 | Haller et al. | |
| 6,890,306 B2 | 5/2005 | Poezevera | |
| 6,978,182 B2 | 12/2005 | Mazar et al. | |
| 7,146,206 B2 | 12/2006 | Glass et al. | |
| 7,395,117 B2 | 7/2008 | Mazar et al. | |
| 7,559,903 B2 | 7/2009 | Moussavi et al. | |
| 7,751,876 B2 | 7/2010 | Healey | |
| 7,787,946 B2 | 8/2010 | Stahmann et al. | |
| 7,996,074 B2 | 8/2011 | Kenknight et al. | |
| 8,002,553 B2 | 8/2011 | Hatlestad et al. | |
| 8,049,489 B2 | 11/2011 | Gauglitz et al. | |
| 8,108,048 B2 | 1/2012 | Masoud | |
| 8,126,548 B2 | 2/2012 | Ding et al. | |
| 8,145,590 B2 | 3/2012 | Brockway et al. | |
| 8,209,011 B2 | 6/2012 | Freeberg | |
| 8,396,543 B2 | 3/2013 | Hoeppner et al. | |
| 8,423,142 B2 | 4/2013 | Freeberg | |
| 8,611,000 B2 | 12/2013 | Komatsu et al. | |
| 8,639,318 B2 | 1/2014 | Hatlestad et al. | |
| 8,694,116 B2 | 4/2014 | Kenknight et al. | |
| 8,731,661 B2 | 5/2014 | White | |
| 8,791,815 B2 | 7/2014 | Mazar et al. | |
| 8,849,682 B2 | 9/2014 | Mahajan et al. | |
| 8,915,741 B2 | 12/2014 | Hatlestad et al. | |
| 8,929,981 B2 | 1/2015 | Perschbacher et al. | |
| 8,983,603 B2 | 3/2015 | Perschbacher et al. | |
| 8,983,620 B2 * | 3/2015 | Cinbis ................ A61N 1/37276 607/60 | |
| 9,014,807 B2 | 4/2015 | Bocek et al. | |
| 9,020,602 B2 | 4/2015 | Aghassian | |
| 9,037,240 B2 | 5/2015 | Gunderson | |
| 9,610,025 B2 | 4/2017 | Zhang | |
| 2001/0051787 A1 | 12/2001 | Haller et al. | |
| 2002/0072783 A1 | 6/2002 | Goedeke et al. | |
| 2003/0028080 A1 | 2/2003 | Lebel et al. | |
| 2005/0042589 A1 | 2/2005 | Hatlestad et al. | |
| 2005/0251227 A1 | 11/2005 | Khoo et al. | |
| 2005/0288599 A1 | 12/2005 | MacAdam et al. | |
| 2006/0241708 A1 | 10/2006 | Boute | |
| 2007/0255330 A1 | 11/2007 | Lee et al. | |
| 2007/0286469 A1 | 12/2007 | Yamagata et al. | |
| 2008/0183245 A1 | 7/2008 | van Oort et al. | |
| 2009/0058635 A1 | 3/2009 | LaLonde et al. | |
| 2009/0063187 A1 | 3/2009 | Johnson et al. | |
| 2009/0088821 A1 | 4/2009 | Abrahamson | |
| 2010/0057167 A1 | 3/2010 | Evers et al. | |
| 2010/0152815 A1 | 6/2010 | Vandanacker | |
| 2010/0185251 A1 | 7/2010 | Propato | |
| 2010/0241182 A1 | 9/2010 | Whitman et al. | |
| 2010/0280841 A1 | 11/2010 | Dong et al. | |
| 2011/0046698 A1 | 2/2011 | Kivi et al. | |
| 2011/0270109 A1 | 11/2011 | Zhang et al. | |
| 2012/0029373 A1 | 2/2012 | Stadler et al. | |
| 2012/0078131 A1 | 3/2012 | Zong | |
| 2012/0154152 A1 | 6/2012 | Rantala et al. | |
| 2012/0165887 A1 | 6/2012 | Lee et al. | |
| 2012/0188096 A1 | 7/2012 | Corndorf et al. | |
| 2012/0232416 A1 | 9/2012 | Gilham et al. | |
| 2012/0253207 A1 | 10/2012 | Sarkar et al. | |
| 2012/0283544 A1 | 11/2012 | Kraetschmer et al. | |
| 2012/0296228 A1 | 11/2012 | Zhang et al. | |
| 2013/0144178 A1 | 6/2013 | Halperin et al. | |
| 2013/0237773 A1 | 9/2013 | An et al. | |
| 2013/0274624 A1 | 10/2013 | Mahajan et al. | |
| 2014/0277243 A1 | 9/2014 | Maskara et al. | |
| 2014/0277286 A1 * | 9/2014 | Cinbis ................ A61N 1/37276 607/60 | |
| 2015/0216433 A1 | 8/2015 | Thakur et al. | |
| 2015/0282738 A1 | 10/2015 | Thakur et al. | |
| 2015/0342487 A1 | 12/2015 | Thakur et al. | |
| 2016/0045125 A1 | 2/2016 | Krueger et al. | |
| 2018/0220373 A1 | 8/2018 | Arzelier et al. | |

OTHER PUBLICATIONS

Passman, Rod S., et al. "Development and Validation of a Dual Sensing Scheme to Improve Accuracy of Bradycardia and Pause Detection in an Insertable Cardiac Monitor." Heart Rhythm, 14:1016-1023, 2017.

Sarkar, Shantanu, et al. "A Dual Sensing Scheme to Reduce Inappropriate Detection of Bradycardia and Pauses in an Insertable Cardiac Monitor." 2016 Heart Rhythm, 15 pages.

International Search Report and Written Opinion issued in PCT/US2017/012641, dated Apr. 24, 2017, 14 pages.

International Search Report and Written Opinion issued in PCT/US2017/012649, dated Mar. 29, 2017, 18 pages.

International Search Report and Written Opinion issued in PCT/US2017/012651, dated Mar. 24, 2017, 12 pages.

International Preliminary Report on Patentability issued in PCT/US2017/012641, dated Jul. 19, 2018, 9 pages.

International Preliminary Report on Patentability issued in PCT/US2017/012649, dated Jul. 19, 2018, 10 pages.

International Preliminary Report on Patentability issued in PCT/US2017/012651, dated Jul. 19, 2018, 8 pages.

International Preliminary Report on Patentability issued in PCT/US2017/020831, dated Sep. 13, 2018, 7 pages.

* cited by examiner

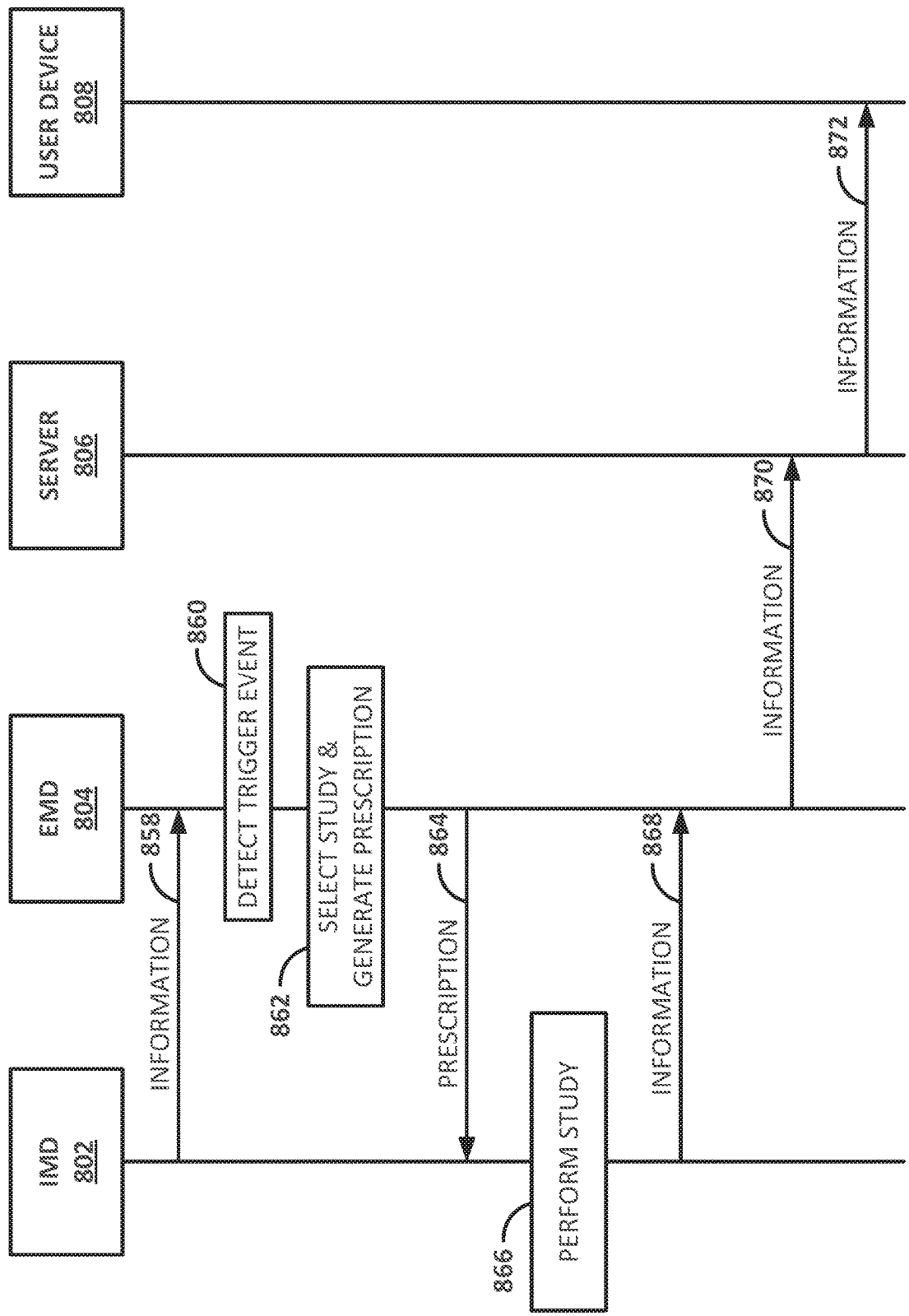

OBTAINING HIGH-RESOLUTION INFORMATION FROM AN IMPLANTABLE MEDICAL DEVICE

CROSS-REFERENCE TO RELATED APPLICATION

This application claims priority to Provisional Application No. 62/276,383, filed Jan. 8, 2016, which is herein incorporated by reference in its entirety.

TECHNICAL FIELD

Embodiments of the present disclosure relate to medical devices and methods for obtaining information. More specifically, embodiments of the disclosure relate to obtaining information using implantable medical devices.

BACKGROUND

Conventional implantable medical devices (IMDs) take frequent physical and device sensor measurements (e.g., once a cardiac cycle, every 50 ms, 5 ms, 2.5 ms, etc.) and use that data to deliver closed loop therapy. However, once data has been used for closed-loop therapy, it is typically discarded or aggregated into a counter, histogram, or index, leaving large amounts of valuable information and/or context unavailable for analysis. This discarding or aggregating of higher-resolution information may be due, for example, to limited memory in the IMD. Additionally, diagnostic analysis often is not performed by an IMD due to limited processing bandwidth, limited power supply, and/or the like.

Although some higher-resolution information may be transmitted from an IMD during a programmer session (e.g., via inductive, conductive, or radio frequency (RF) telemetry), the amount of data captured typically is fairly limited. For example, an hour of continuous RF telemetry may reduce the longevity of an IMD by about 9 days. Similarly, 8 hours of continuous RF telemetry (e.g., during a sleep study) may have a longevity impact of about 72 days (0.2 years) on an IMD; 24 hours of continuous RF telemetry (e.g., during a Holter study) may have a longevity impact of about 216 days (0.6 years); and 14 days (336 hours) of continuous RF telemetry (e.g., during an atrial fibrillation monitoring session) may have a longevity impact of about 3,024 days (8.3 years). In addition to device longevity concerns, inductive and conductive telemetry also requires proximity of the devices involved (e.g., external devices must be kept close to, or in contact with, the body for communicating with IMDs).

SUMMARY

Embodiments of the disclosure include systems and methods for obtaining high-resolution data from implantable medical devices (IMDs) by obtaining, communicating, and/or analyzing information in accordance with a study prescription. The study prescription is generated in such a way as to obtain useful data while mitigating potential impact on the longevity of one or more components of the IMD.

In an Example 1, a system comprises: an implantable medical device (IMD) configured to be implanted within a patient's body, the IMD comprising: a sensing component configured to obtain values of a first physiological parameter; a power source configured to provide power to the IMD; and a first communication component configured to transmit, according to a study prescription, the values of the first physiological parameter, the study prescription comprising a communication scheme that is configured based on an impact on a longevity of at least one component of the IMD; and an external monitoring device (EMD) configured to be disposed outside of a patient's body, the EMD comprising a second communication component, configured to receive, from the first communication component, the values of the first physiological parameter.

In an Example 2, the system of Example 1, wherein the study prescription further includes instructions configured to cause the sensing component to store the values of the first physiological parameter, to cause the first communication component of the IMD to transmit the first set of information to the second communication component, to transmit the first set of information to the second communication component using a burst transfer, to transmit the first set of information to the second communication component using a streaming communication, to transmit the first set of information to the second communication component for a specified period of time, to store a portion of the first set of information, to enable one or more sensing components, to modify a sampling rate or a sample storage rate of the one or more sensing components (which may, in embodiments, include memory), and/or the like.

In an Example 3, the system of any of Examples 1 and 2, wherein the impact on the longevity of the at least one component of the IMD corresponds to an amount of power consumption associated with the information transmission.

In an Example 4, the system of any of Examples 1-3, wherein the impact on the longevity of the at least one component of the IMD corresponds to at least one of an amount of power consumption associated with obtaining the values of the first physiological parameter and storing the values of the first physiological parameter.

In an Example 5, the system of any of Examples 1-4, the IMD further comprising a trigger component configured to detect, based on a first set of information, a trigger event, wherein the first set of information comprises a set of values of a second physiological parameter.

In an Example 6, the system of any of Examples 1-4, the EMD further comprising a trigger component configured to detect, based on a first set of information, a trigger event, wherein the first set of information comprises values of a second physiological parameter.

In an Example 7, the system of any of Examples 5 and 6, the values of the second physiological parameter comprising additional values of the first physiological parameter. In embodiments, the additional values of the first physiological parameter may be obtained using a different (e.g. a higher) sampling rate, may be stored using a different (e.g., a higher) sample storage rate, may be streamed to the second device, and/or the like.

In an Example 8, the system of any of Examples 1-7, further comprising a management server, the management server comprising a third communication component configured to communicate with the second communication component.

In an Example 9, the system of any of Examples 1-8, wherein at least one of the EMD and management server provides an analysis component configured to analyze at least the values of the first physiological parameter.

In an Example 10, the system of Example 9, wherein the analysis component is configured to implement one or more adjudication algorithms to adjudicate a diagnosis based on the values of the first physiological parameter.

In an Example 11, the system of any of Examples 1-10, wherein at least one of the IMD, EMD, and management server implements a prescription component, the prescription component configured to enable implementation of the study prescription.

In an Example 12, the system of Example 11, the prescription component comprising: a study selection component configured to select a diagnostic model from among a plurality of candidate diagnostic models; and a prescription generator configured to generate the study prescription based on the selected diagnostic model.

In an Example 13, the system of any of Examples 8-12, wherein the management server further comprises a confirmation component configured to provide a notification of the study prescription to a user device, and to receive, from the user device, at least one of a confirmation of the study prescription or a modification of the study prescription. In embodiments, the confirmation of the study prescription may include an approval of the study prescription, a user instruction to implement the study prescription, and/or the like. The modification of the study prescription may include an instruction from the user to alter one or more components of the study prescription.

In an Example 14, a method of managing communication of values of a first physiological parameter sensed by an implantable medical device (IMD) to an external monitoring device (EMD) comprises: obtaining a first set of information, the first set of information comprising at least one value of an IMD parameter associated with power consumption; generating a study prescription, the study prescription comprising a communication scheme that is configured based on power consumption; and facilitating transmission, according to the study prescription, of the values of the first physiological parameter from the IMD to the EMD.

In an Example 15, the method of Example 14, further comprising: obtaining a first set of information comprising at least one value of a second physiological parameter; and detecting, based on the first set of information, a trigger event, wherein the step of generating the study prescription is performed in response to detecting the trigger event.

In an Example 16, a system comprises: an implantable medical device (IMD) configured to be implanted within a patient's body, the IMD comprising: a sensing component configured to obtain values of a first physiological parameter; a power source configured to provide power to the IMD; and a first communication component configured to transmit, according to a study prescription, the values of the first physiological parameter, the study prescription comprising a communication scheme that is configured based on an impact on a longevity of at least one component of the IMD; and an external monitoring device (EMD) configured to be disposed outside of a patient's body, the EMD comprising a second communication component, configured to receive, from the first communication component, the values of the first physiological parameter.

In an Example 17, the system of Example 16, wherein the impact on the longevity of the at least one component of the IMD corresponds to an amount of power consumption associated with the information transmission.

In an Example 18, the system of Example 16, wherein the study prescription further includes instructions configured to cause the sensing component to store the values of the first physiological parameter.

In an Example 19, the system of Example 18, wherein the impact on the longevity of the at least one component of the IMD corresponds to at least one of an amount of power consumption associated with obtaining the values of the first physiological parameter and storing the values of the first physiological parameter.

In an Example 20, the system of Example 18, the IMD further comprising a trigger component configured to detect, based on a first set of information, a trigger event, wherein the first set of information comprises a set of values of a second physiological parameter.

In an Example 21, the system of Example 18, the EMD further comprising a trigger component configured to detect, based on a first set of information, a trigger event, wherein the first set of information comprises values of a second physiological parameter.

In an Example 22, the system of Example 18, the values of the second physiological parameter comprising additional values of the first physiological parameter.

In an Example 23, the system of Example 16, further comprising a management server, the management server comprising a third communication component configured to communicate with the second communication component.

In an Example 24, the system of Example 23, wherein at least one of the EMD and management server provides an analysis component configured to analyze at least the values of the first physiological parameter.

In an Example 25, the system of Example 24, wherein the analysis component is configured to implement one or more adjudication algorithms to adjudicate a diagnosis based on the values of the first physiological parameter.

In an Example 26, system of Example 25, wherein at least one of the IMD, EMD, and management server implements a prescription component, the prescription component configured to enable implementation of the study prescription.

In an Example 27, the system of Example 26, the prescription component comprising: a study selection component configured to select a diagnostic model from among a plurality of candidate diagnostic models; and a prescription generator configured to generate the study prescription based on the selected diagnostic model.

In an Example 28, the system of Example 23, wherein the management server further comprises a confirmation component configured to provide a notification of the study prescription to a user device, and to receive, from the user device, at least one of a confirmation of the study prescription or a modification of the study prescription.

In an Example 29, a method of managing communication of values of a first physiological parameter sensed by an implantable medical device (IMD) to an external monitoring device (EMD) comprises: obtaining a first set of information, the first set of information comprising at least one value of an IMD parameter associated with power consumption; generating a study prescription, the study prescription comprising a communication scheme that is configured based on power consumption; and facilitating transmission, according to the study prescription, of the values of the first physiological parameter from the IMD to the EMD.

In an Example 30, the method of Example 29, further comprising: obtaining a first set of information comprising at least one value of a second physiological parameter; and detecting, based on the first set of information, a trigger event, wherein the step of generating the study prescription is performed in response to detecting the trigger event.

In an Example 31, the method of Example 30, wherein generating the study prescription comprises: identifying, based on the first set of information, a plurality of diagnostic models; determining, for each of the plurality of diagnostic models, one or more input options; calculating, for each of the plurality of diagnostic models, a cost associated with each of the one or more input options; selecting, based on the calculated cost associated with each of the one or more input options, one of the plurality of diagnostic models, wherein the selected diagnostic model comprises a set of inputs; establishing a set of input parameters associated with the set of inputs; and generating, based on the set of input parameters, a set of instructions configured to be executed by the IMD to implement the study prescription.

In an Example 32, a system comprises: an implantable medical device (IMD) configured to be implanted within a patient's body, the IMD comprising: a sensing component configured to (1) obtain a first set of values of a first physiological parameter, and (2) obtain, according to a study prescription, a second set of values of a second physiological parameter; a first communication component configured to transmit the first set of values of the first physiological parameter and the second set of values of the second physiological parameter; a trigger notification, the trigger notification comprising an indication of the detection of the trigger event; an external monitoring device (EMD) configured to be disposed outside of a patient's body, the EMD comprising: a second communication component, configured to receive, from the first communication component, the first set of values of the first physiological parameter, the second set of values of the second physiological parameter, and a first set of information, the first set of information comprising a value of at least one IMD parameter; a trigger component configured to detect, based on the first set of values of the first physiological parameter, a trigger event; and a prescription component configured to generate, based on the trigger event and the value of the at least one IMD parameter, a study prescription, wherein the second communication component is further configured to transmit the study prescription to the first communication component; the study prescription comprising a communication scheme that is configured based on an impact on a longevity of at least one component of the IMD.

In an Example 33, the system of Example 32, wherein the impact on the longevity of the at least one component of the IMD corresponds to an amount of power consumption associated with the information transmission.

In an Example 34, the system of Example 33, wherein the impact on the longevity of the at least one component of the IMD further corresponds to at least one of an amount of power consumption associated with obtaining the second set of values of the second physiological parameter and storing the second set of values of the second physiological parameter.

In an Example 35, the system of Example 32, wherein at least one of the EMD and a management server provides an analysis component configured to analyze at least the values of the first physiological parameter, wherein the analysis component is configured to implement one or more adjudication algorithms to adjudicate a diagnosis based on the values of the first physiological parameter.

While multiple embodiments are disclosed, still other embodiments of the presently disclosed subject matter will become apparent to those skilled in the art from the following detailed description, which shows and describes illustrative embodiments of the disclosed subject matter. Accordingly, the drawings and detailed description are to be regarded as illustrative in nature and not restrictive.

BRIEF DESCRIPTION OF THE DRAWINGS

FIGS. 8A, 8B, and 8C depict illustrative communication flows among an IMD 802, an EMD 802, a server 806, and a user device 808, in accordance with embodiments of the disclosure.

Figure 1:
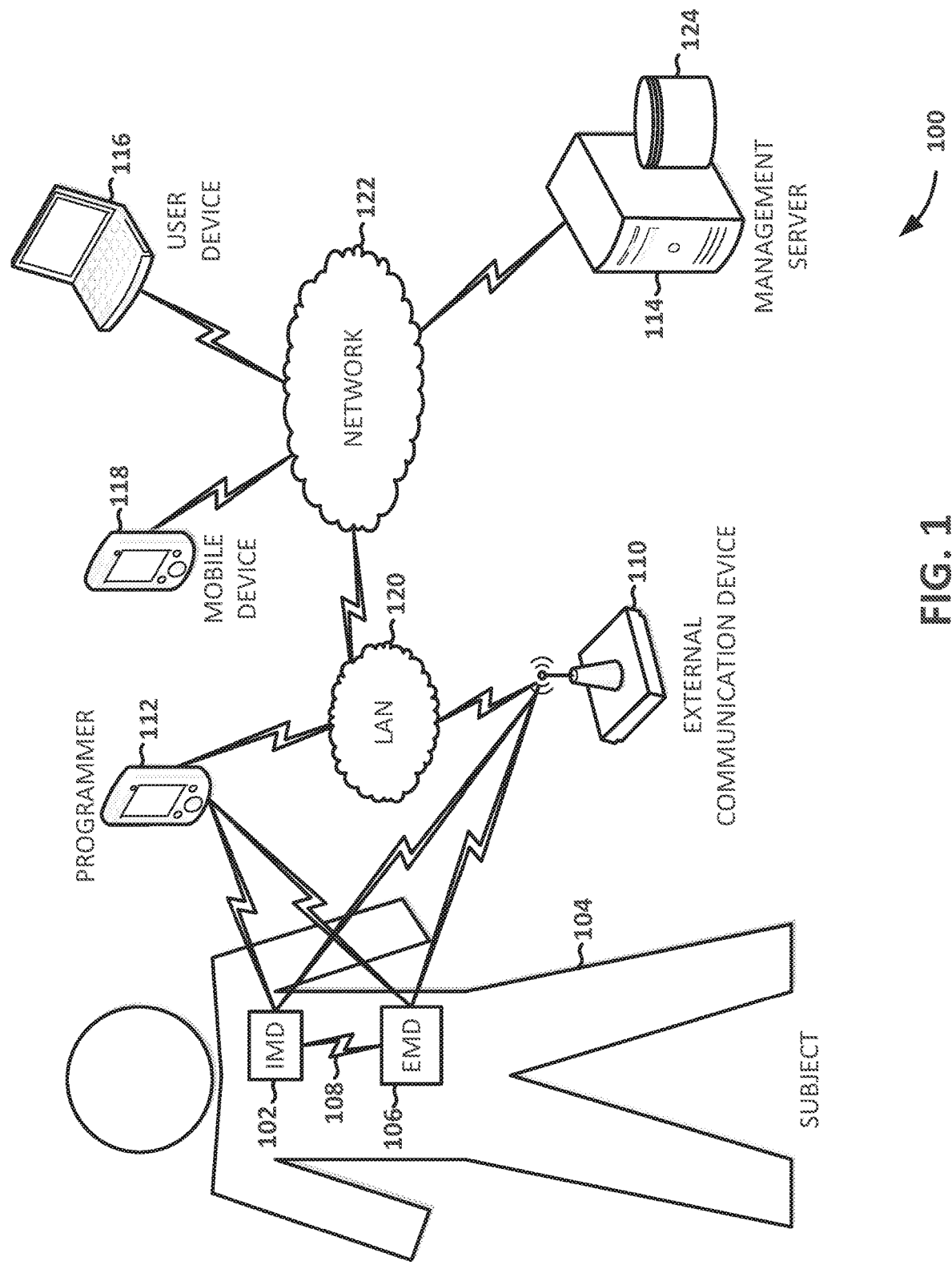
FIG. 1 is a schematic drawing of an illustrative medical system 100, in accordance with embodiments of the disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps. Additionally, a "set" or "group" of items (e.g., inputs, algorithms, data values, etc.) may include one or more items, and, similarly, a subset or subgroup of items may include one or more items.

DETAILED DESCRIPTION

Embodiments of the disclosure include systems and methods for obtaining data from implantable medical devices (IMDs). In embodiments, data is obtained from an IMD by triggering a limited-time system behavior change. Embodiments include utilizing study prescriptions that specify one or more criteria, procedures, parameters, and/or other aspects of obtaining the data. For example, study prescriptions may facilitate enabling sensor components, obtaining data, analyzing data, batching data obtained by an IMD, communicating the batched data to an external device, reconstructing the batched data at the external device, and/or the like. Study prescriptions may also include instructions for configuring one or more sensors, modifying one or more filters, modifying one or more sensor inputs (e.g. by changing a vector measured by a minute volume (MV) impedance component from focusing on changes in a lung to focusing on stroke volume of the heart), modifying one or more sensing parameters (e.g., sampling rate, sample storage rate, sensing thresholds, sensing durations, etc.), and/or the like. Study prescriptions refer to sets of instructions, conditions, protocols, and/or the like, that specify one or more of an information gathering scheme and a communication scheme, and may be configured, for example, to obtain information at a resolution sufficient for performing a certain analysis (e.g., associated with a diagnostic model), while managing the resulting impact to device longevity and/or performance.

In this manner, for example, a particular sensor may be generally disabled (e.g., because it consumes relatively large amounts of power, is not necessary for a day-to-day or beat-to-beat operation, etc.), but may be able to be enabled in response to execution of instructions of a study prescription. For example, in embodiments, the filters of an accelerometer may be modified, according to a study prescription, to analyze data in different frequency ranges. In an implementation, for example, an IMD may be configured to generally use an accelerometer to drive rate and sample sensed measurements in a first frequency range, e.g., to facilitate rate-responsive pacing. A study prescription may be configured to cause the IMD to perform a sleep apnea study overnight and, accordingly, may cause the IMD to sample sensed measurements in a second frequency range so that the IMD can detect throat sounds. In this example, the study prescription may also be configured to disable the rate-responsive pacing functions during the night-time sleep study.

For example, a study prescription for a Holter study might include a communication scheme that, when implemented by an IMD, causes the IMD to batch information and transmit the batches once per hour. In conventional IMDs, nearly an hour's worth of single-channel EGM samples along with device-determined information markers can be transmitted in about one minute's worth of RF telemetry. Embodiments of the disclosure facilitate a managed batch approach to transmitting this data, which may result in substantially less longevity impact compared to the approximately 9 days of longevity impact on a conventional IMD for one hour of continuous RF telemetry to obtain the same data (or approximately 72 days of longevity impact for the typical 24 hour duration of a Holter study).

Thus, in the case of, for example, a 10-year IMD, the longevity impact of batching 8 hours of telemetry (e.g., for a sleep study) may be less than a day and a half; the longevity impact of batching 24 hours of telemetry (e.g., for a pacing effectiveness study) may be about 3 to 4 days; the longevity impact of batching 14 days (336 hours) of telemetry (e.g., for an atrial fibrillation monitoring study) may be about 51 days (0.14 years); and the longevity impact of batching 90 days (2,160 hours) of telemetry (e.g., for an atrial fibrillation monitoring study) may be about 329 days (0.9 days). In this manner, embodiments may facilitate reducing longevity impacts on IMDs, thus enabling clinicians to more feasibly and/or ethically obtain this type of information.

In embodiments, a clinician may determine a need or desire for obtaining data (information) from an IMD and may discuss this need for the data with the patient, after which the clinician may "prescribe" the data gathering study. The patient's implanted device may be set up to transmit data for prescribed period of time (e.g., automatically, via a wearable external monitoring device). The data may be, for example, transmitted in a continuous RF communication, batched, and/or the like. In embodiments, batching data may be dependent on a multitude of factors, e.g., the studies conducted, what channels are recording by default, whether any channels kick in after the first channel records something of interest for a study, and/or the like.

Embodiments may include any number of different considerations that may facilitate maximizing (or at least enhancing) data gathering while minimizing (or at least reducing) resulting impacts on the longevity of one or more components of the IMD. Such considerations may include, for example, storage capacity, power source depletion; and/or the like. Any number of various techniques may be implemented to facilitate these and/or other objectives. For example, rolling buffers may be implemented for managing the stored information. In embodiments, data may be overlapped to account for missed transmissions, such that when external devices piece the data back together (e.g., based on time stamps), the data is complete, and repeated data can be discarded. Data may also be synchronized with data from other sensors so that one parameter may be analyzed in the context of one or more other parameters. Any number of techniques for synchronizing data may be utilized including, for example, using sync signals as described in U.S. Provisional Application No. 62/276,686, titled "SYNCING MULTIPLE SOURCES OF PHYSIOLOGICAL DATA," filed Jan. 8, 2016, the disclosure of which is hereby incorporated by reference herein in its entirety. In embodiments, the IMD may be configured to sense information at a lower resolution unless a trigger event (described in more detail below) is detected, at which time data may be gathered at a higher resolution. In embodiments, an external device may be passive and/or may actively request data from the IMD.

In embodiments, the number of times a study prescription can be enabled may be limited by the prescription, the IMD, the external device, and/or the like. In embodiments, a study prescription may also cause an IMD to provide information associated with the cumulative impact to the longevity of the IMD from implementing the study prescription, and may prompt a server or other device to obtain confirmation from a user before authorizing implementation of another study prescription, or another implementation of the same study prescription. Similarly, the IMD may perform a study prescription in stages, providing longevity impact information after the completion of each stage (with the system, perhaps, requiring a user confirmation to continue with the study prescription after each stage).

Additionally, to enhance efficiency, a study prescription may cause an IMD to turn off one or more channels when the IMD is gathering data. In embodiments, the study prescription may be configured to cause the IMD to first obtain the information that has the lowest longevity impact cost initially and then to dynamically determine how much additional information is needed, as captured information is analyzed. Embodiments may also facilitate dynamically switching frequencies at which communications are conducted, dynamically adjusting data sampling rates, data batching frequencies, and/or the like. Additionally, embodiments may facilitate remotely programming IMDs (e.g., to be remotely turned off, to remotely enable study prescriptions, to remotely adjust therapy, and/or the like).

FIG. 1 shows an illustrative medical system 100, in accordance with embodiments of the disclosure. As shown in FIG. 1, the medical system 100 includes an IMD 102 configured to be implanted within the body of a subject 104, and an external monitoring device (EMD) 106, which is communicatively coupled to the IMD 102 via a communication link 108. In the illustrated embodiments, the medical system 100 is operatively coupled to the subject 104, and the IMD 102 and the EMD 106 are configured to communicate with one another over the communication link 108. The subject 104 may be a human, a dog, a pig, and/or any other animal having physiological parameters that can be recorded. For example, in embodiments, the subject 104 may be a human patient.

In embodiments, the communication link 108 may be, or include, a wireless communication link such as, for example, a short-range radio link, such as Bluetooth, IEEE 802.11, a proprietary wireless protocol, and/or the like. In embodiments, for example, the communication link 108 may utilize Bluetooth Low Energy radio (Bluetooth 4.1), or a similar protocol, and may utilize an operating frequency in the range of 2.40 to 2.48 GHz. The term "communication link" may refer to an ability to communicate some type of information in at least one direction between at least two devices, and should not be understood to be limited to a direct, persistent, or otherwise limited communication channel. That is, according to embodiments, the communication link 108 may be a persistent communication link, an intermittent communication link, an ad-hoc communication link, and/or the like. The communication link 108 may refer to direct communications between the IMD 102 and the EMD 106, and/or indirect communications that travel between the IMD 102 and the EMD 106 via at least one other device (e.g., a repeater, router, hub, and/or the like). The communication link 108 may facilitate uni-directional and/or bi-directional communication between the IMD 102 and the EMD 106. Data and/or control signals may be transmitted between the IMD 102 and the EMD 106 to coordinate the functions of the IMD 102 and/or the EMD 106. In embodiments, patient data may be downloaded from one or more of the IMD 102 and the EMD 106 periodically or on command. The physician and/or the patient may communicate with the IMD 102 and the EMD 106, for example, to acquire patient data or to initiate, terminate and/or modify recording and/or therapy.

In embodiments, the IMD 102 and/or the EMD 106 may provide one or more of the following functions with respect to a patient: sensing, data analysis, and therapy. For example, in embodiments, the IMD 102 and/or the EMD 106 may be used to measure any number of a variety of physiological, device, subjective, and/or environmental parameters associated with the subject 104, using electrical, mechanical, and/or chemical means. The IMD 102 and/or the EMD 106 may be configured to automatically gather data, gather data upon request (e.g., input provided by the subject, a clinician, another device, and/or the like), and/or any number of various combinations and/or modifications thereof. The IMD 102 and/or EMD 106 may be configured to store data related to the physiological, device, environmental, and/or subjective parameters and/or transmit the data to any number of other devices in the system 100. In embodiments, the IMD 102 and/or the EMD 106 may be configured to analyze data and/or act upon the analyzed data. For example, the IMD 102 and/or EMD 106 may be configured to modify therapy, perform additional monitoring, and/or provide alarm indications based on the analysis of the data.

In embodiments, the IMD 102 and/or the EMD 106 may be configured to provide therapy. Therapy may be provided automatically and/or upon request (e.g., an input by the subject 104, a clinician, another device or process, and/or the like). The IMD 102 and/or the EMD 106 may be programmable in that various characteristics of their sensing, therapy (e.g., duration and interval), and/or communication may be altered by communication between the devices 102 and 106 and/or other components of the system 100.

According to embodiments, the IMD 102 may include any type of IMD, any number of different components of an implantable system, and/or the like. For example, the IMD 102 may include a control device, a monitoring device, a pacemaker, an implantable cardioverter defibrillator (ICD), a cardiac resynchronization therapy (CRT) device and/or the like, and may be an implantable medical device known in the art or later developed, for providing therapy and/or diagnostic data about the subject 104 and/or the IMD 102. In various embodiments, the IMD 102 may include both defibrillation and pacing/CRT capabilities (e.g., a CRT-D device).

In embodiments, the IMD 102 may be implanted subcutaneously within an implantation location or pocket in the patient's chest or abdomen and may be configured to monitor (e.g., sense and/or record) physiological parameters associated with the patient's heart. In embodiments, the IMD 102 may be an implantable cardiac monitor (ICM) (e.g., an implantable diagnostic monitor (IDM), an implantable loop recorder (ILR), etc.) configured to record physiological parameters such as, for example, one or more cardiac electrical signals, heart sounds, heart rate, blood pressure measurements, oxygen saturations, and/or the like.

In embodiments, the IMD 102 may be configured to monitor physiological parameters that may include one or more signals indicative of a patient's physical activity level and/or metabolic level, such as an acceleration signal. In embodiments, the IMD 102 may be configured to monitor physiological parameters associated with one or more other organs, systems, and/or the like. The IMD 102 may be configured to sense and/or record at regular intervals, continuously, and/or in response to a detected event. For example, in embodiments, the IMD 102 may be configured to detect a trigger event (described in more detail below) and communicate a notification of the trigger event to the EMD 106, which may perform one or more actions to enable a study prescription that may be implemented by the IMD 102 to acquire higher resolution data to confirm the trigger event, classify the trigger event, diagnose a related condition, and/or the like.

In addition, the IMD 102 may be configured to detect a variety of physiological signals that may be used in connection with various diagnostic, therapeutic and/or monitoring implementations. For example, the IMD 102 may include sensors or circuitry for detecting respiratory system signals, cardiac system signals, heart sounds. and/or signals related to patient activity. In embodiments, the IMD 102 may be configured to sense intrathoracic impedance, from which various respiratory parameters may be derived, including, for example, respiratory tidal volume and minute ventilation. Sensors and associated circuitry may be incorporated in connection with the IMD 102 for detecting one or more body movement or body posture and/or position related signals. For example, accelerometers and/or GPS devices may be employed to detect patient activity, patient location, body orientation, and/or torso position.

Derived parameters may also be monitored using the IMD 102. For example, a sleep sensor may rely on measurements taken by an implanted accelerometer that measures body activity levels. The sleep sensor may estimate sleeping patterns based on the measured activity levels. Other derived parameters include, but are not limited to, a functional capacity indicator, autonomic tone indicator, sleep quality indicator, cough indicator, anxiety indicator, and a cardiovascular wellness indicator for calculating a quality of life indicator quantifying a subject's overall health and well-being.

In various embodiments, the EMD 106 may be a device that is configured to be portable with the subject 104, e.g., by being integrated into a vest, belt, harness, sticker; placed into a pocket, a purse, or a backpack; carried in the subject's hand; and/or the like, or otherwise operatively (and/or physically) coupled to the subject 104. The EMD 106 may be configured to monitor (e.g., sense and/or record) physiological parameters associated with the subject 104 and/or provide therapy to the subject 104. For example, the EMD 106 may be, or include, a wearable cardiac defibrillator (WCD) such as a vest that includes one or more defibrillation electrodes. In embodiments, the EMD 106 may include any number of different therapy components such as, for example, a defibrillation component, a drug delivery component, a neurostimulation component, a neuromodulation component, a temperature regulation component, and/or the like. In embodiments, the EMD 106 may include limited functionality, e.g., defibrillation shock delivery and communication capabilities, with arrhythmia detection, classification and/or therapy command/control being performed by a separate device such as, for example, the IMD 102.

In embodiments, the EMD 106 may include sensing components such as, for example, one or more surface electrodes configured to obtain an electrocardiogram (ECG), one or more electrodes configured to obtain an electronystagmogram (ENG), one or more electrodes configured to obtain an electroencephalogram (EEG), one or more accelerometers configured to detect motion associated with the patient 104, one or more respiratory sensors configured to obtain respiration information, one or more environmental sensors configured to obtain information about the external environment (e.g., temperature, air quality, humidity, carbon monoxide level, oxygen level, barometric pressure, light intensity, sound, and/or the like) surrounding the patient 104, and/or the like. In embodiments, the EMD 106 may be configured to measure parameters relating to the human body, such as temperature (e.g., a thermometer), blood pressure (e.g., a sphygmomanometer), blood characteristics (e.g., glucose levels), body weight, physical strength, mental acuity, diet, heart characteristics, relative geographic position (e.g., a Global Positioning System (GPS)), and/or the like.

According to embodiments, the EMD 106 may be configured to measure subjective and/or perceptive data from the subject 104. Subjective data is information related to a patient's feelings, perceptions, and/or opinions, as opposed, for example, to objective physiological data. For example, EMD 106 may be configured to measure subject responses to inquiries such as "How do you feel?" and "How is your pain?" The EMD 106 may be configured to prompt the subject 104 and record subjective data from the subject 104 using visual and/or audible cues. In embodiments, the subject 104 can press coded response buttons or type an appropriate response on a keypad. In embodiments, subjective data may be collected by allowing the subject 104 to speak into a microphone and using speech recognition software to process the subjective data.

In embodiments, the EMD 106 may include a prescription enabler (discussed in further detail below) that may be configured to automatically enable a study prescription when the EMD 106 is within communicating range of the IMD 102. In embodiments, enablement of the study prescription may require a password or other input, which may be received by the EMD 106. In other embodiments, the EMD 106 may include a button, switch, or other actuable mechanism that a patient or clinician may actuate to enable the study prescription. In other embodiments, the study prescription may be enabled at an earlier time (e.g., in the clinician's office, using a wand), but implemented later, in response to an input from the subject indicating, for example, that the subject is going to bed, having a certain feeling, and/or the like. In embodiments, the study prescription may be enabled within the IMD 102 earlier (e.g., in the clinician's office), and implemented only when the subject comes into proximity of the EDM 106 (or enabled within the IMD 102 and/or EMD 106 and implemented when the subject comes into proximity of another external device such as, for example, an external communication device 110).

As shown in FIG. 1, the system 100 includes the external communication device 110 and a programmer 112. In embodiments, the external communication device 110 and/or the programmer 112 may be, be similar to, include, or be included in, the EMD 106, while in other embodiments, the external communication device 110 and/or the programmer 112 may be separate devices from the EMD 106. In embodiments, the external communication device 110 and/or the programmer 112 may be provided to the subject 104 and are often located within the subject's home.

According to embodiments, the external communication device 110 and/or the programmer 112 may be configured to send data to, and receive data from, a device, such as the IMD 102, the EMD 106, the other of the external communication device 110 and the programmer 112, and/or any number of other devices depicted or not depicted in FIG. 1. Such communications may be facilitated via communication links 108B-108I, any number of which may be, be identical to, be similar to, include, be coupled with, or be included within, the communication link 108A. The external communication device 110 and/or programmer 112 may operate as an interrogator of the IMD 102 and/or the EMD 106. In embodiments, the external communication device 110 and/or programmer 112 may perform one or more of the following functions: (1) data storage; (2) data analysis; (3) data forwarding; (4) patient interaction; (5) patient feedback; and (6) data communications. For example, the external communication device 110 and/or programmer 112 may facilitate communications between the devices 102 and 106 and a management server 114, a user device 116, a mobile device 118, and/or the like. The external communication device 110 and/or programmer 112 may, periodically or in real-time, interrogate and download into memory clinically relevant patient data. This data may include, for example, P and R-wave measurements, pacing, cardiac event interval information, shocking events, lead impedances, pacing thresholds, battery voltage, capacitor charge times, ATR episodes with electrograms, tachycardia episodes with electrograms, histogram information, and/or any other clinical information necessary to ensure patient health and proper device function.

The external communication device 110 and/or programmer 112 may also allow subject (e.g., patient) interaction. For example, the external communication device 110 and/or programmer 112 may include a patient interface and allow the patient to input subjective data. In addition, the external communication device 110 and/or programmer 112 may provide feedback to the patient based on the data that has been analyzed or based on information communicated by the management server 114.

In embodiments, the external communication device 110 and/or programmer 112 may communicate with a network 120 that may be, for example, a local area network (LAN) in the subject's home or other location. The external communication device 110 and/or programmer 112 may be configured to systematically obtain information from the devices 102 and/or 106 while the patient is sleeping, for example. The obtained data may be transmitted through the network 120 and/or a network 122 to the management server 114. In addition, in embodiments the external communication device 110 and/or programmer 112 functions in a hybrid form, utilizing wireless communication when available and defaulting to a local wireless portal or a wired connection when the wireless communication becomes unavailable. In embodiments, the network 120 and the network 122 may be integrated within one another, may be the same network, and/or the like.

In embodiments, the external communication device 110 and/or programmer 112 may be in the form of a small device that is placed in an inconspicuous place within the subject's residence and may use radio frequency (RF) to communicate with the IMD 102 and/or EMD 106. The external communication device 110 and/or programmer 112 may be implemented as part of a commonly-used appliance in the subject's residence. For example, the external communication device 110 and/or programmer 112 may be integrated with an alarm clock that is positioned near the subject's bed. In another embodiment, the external communication device 110 and/or programmer 112 may be implemented as part of the subject's personal computer system. In another embodiment, the external communication device 110 and/or programmer 112 may include a hand-held device such as a PDA, cellular telephone, or other similar. The hand-held device may upload data to the management server 114 wirelessly. Additionally, or alternatively, the hand-held device may periodically be placed in a cradle or other similar device that is configured to transmit the data to the management server 114. In embodiments, the external communication device 110 and/or programmer 112 may perform analysis on data and provide immediate feedback, as well as perform a variety of self-diagnostic tests to verify that it is functioning properly and that communication with one or more other devices has not be compromised.

In embodiments of the system 100, one or more functions of the external communication device 110 and/or programmer 112 may be integrated into the IMD 102, the EMD 106, the user device 116, and/or the mobile device 118. In some embodiments, the devices may communicate directly with the management server 114, which may be located in the subject's home and/or at a remote location (e.g., the server 114 may be implemented, at least in part, as software having components instantiated by more than one device). The devices 102, 106, 110, and/or 112 may incorporate multimode wireless telecommunications such as cellular, BLUETOOTH, or IEEE 802.11B to communicate with the networks 120 and/or 122. For example, the EMD 106 may include a miniature cellular phone capable of wirelessly uploading clinical data from the device on a periodic basis.

In embodiments, various devices of the system 100 may be configured to communicate during a given duty cycle. For example, the IMD 102, EMD 106, external communication device 110 and/or programmer 112 may be configured to communicate with the management server 114 (or other device) at given intervals, such as once a week. The IMD 102, EMD 106, external communication device 110 and/or programmer 112 may record data for the time period (e.g., a week) and transmit the data to the management server 114 (or other device) during the portion of the cycle that transmission is active and then conserve energy for the rest of the cycle. In another example, the IMD 102, EMD 106, external communication device 110 and/or programmer 112 conserve energy and only communicates with the management server 114 (or other device) when a trigger event or execution of a study prescription has occurred.

Various components depicted in FIG. 1 may operate together to form the monitoring system 100, which may be, for example, a computerized patient management and monitoring system. In embodiments, the system 100 may be designed to assist in monitoring the subject's condition, managing the subject's therapy, and/or the like. An illustrative patient management and monitoring system is the LATITUDE® patient management system from Boston Scientific Corporation, Natick Mass. Illustrative aspects of a patient management and monitoring system are described in ADVANCED PATIENT MANAGEMENT SYSTEM INCLUDING INTERROGATOR/TRANSCEIVER UNIT, U.S. Pat. No. 6,978,182 to Mazar et al., the entirety of which is hereby incorporated by reference herein.

Patient management and monitoring systems can provide large amounts of data about patients to users such as, for example, clinicians, patients, researchers, and/or the like. For example, such systems can store information about patient characteristics, patient sensor readings including electrocardiograms (EGMs), device settings, therapy deliveries, and/or the like. For example, in embodiments, medical devices such as the IMD 102 and/or the EMD 106 may obtain parameter values that include information associated with an arrhythmia episode or other episode experienced by the patient. As it is used herein, the term "episode" refers to a time period during which some sort of abnormal event occurs. For example, an episode may refer to an arrhythmia, a sleep disturbance (e.g., an apnea episode, a snoring episode, etc.), a psychological episode (e.g., a seizure or other epileptic episode), and/or the like. "Episode data" may include physiological parameter values obtained before, during and/or after an episode, and may also include device settings, actions that were taken by the device, actions that were taken by a user, environmental parameters, and/or other information.

The episode data, or part of the episode data, corresponding to a particular episode may be analyzed using one or more adjudication algorithms to determine one or more classifications of the episode. For example, arrhythmia adjudication algorithms may be used to determine arrhythmia classifications and/or other types of characterizations about an arrhythmia episode; a sleep disturbance adjudication algorithm may be used to determine sleep disturbance classifications and/or other types of characterizations about a sleep disturbance episode; a psychological abnormality adjudication algorithm may be used to determine psychological abnormality classifications and/or other types of characterizations about a psychological episode; and/or the like.

According to embodiments, an adjudication algorithm may be used to detect a particular event, referred to herein as a "trigger event," that prompts further data gathering and analysis (e.g., further adjudications). For example, a medical device (e.g., the IMD 102 and/or the EMD 106) may obtain a first set of information, which may be analyzed to detect a trigger event. The trigger event may be, for example, a certain heart rate, EGM feature, snoring episode, apnea episode, and/or the like. In response to detecting the trigger event, the system may generate a study prescription that, when executed, facilitates enabling the IMD 102 to perform at least a portion of a study. As the term is used herein, a "study" is a monitoring activity that involves obtaining certain parameter values, storing certain parameter values, transmitting certain parameter values, and/or analyzing certain parameter values according to a study prescription, which includes one or more instructions, rules, schemes, and/or the like. For example, in embodiments, a study prescription may include a communication scheme that is configured based on IMD power consumption associated with information transmission from the IMD 102 to an EMD 106 or other device. In executing a study prescription, one or more components of the system 100 obtain and/or store a second set of information that may be analyzed using one or more adjudication algorithms to classify an episode, characterize the condition of a component of the IMD (e.g., a lead integrity), audit the effectiveness of a therapy regimen, and/or the like.

According to embodiments, classifications and/or characterization data can be stored in an adjudication database. In some examples, the characterization data may be sent to the medical device (e.g., IMD 102 and/or EMD 106) to be stored. Once a classification (e.g., an arrhythmia classification) has been generated for a particular episode or a group of episodes, it may be possible to provide patients and/or clinicians with many different types of reports related to the episode data. It may also be possible for the system to analyze the classifications and/or characterization data to provide programming recommendations for a medical device where certain conditions are present. It may also be possible to query the adjudication database for many different types of information that may be useful to clinicians, researchers, regulators, and/or the like.

In embodiments, episode adjudication for detecting a trigger event may be done by the IMD 102 and/or by the EMD 106. For example, a controller or controllers may be configured to extract certain features from a set of information that may include episode data, which may be useful in classifying an episode. The features may, in embodiments, be based on domain knowledge used by clinicians, engineers, technicians, and/or the like to classify the episode data. For example, in embodiments, an electrogram may be used to determine if an arrhythmia episode originates from the atrium or ventricle of the heart through analyzing the timing of the atrial and ventricle activities. The determination can alternatively or additionally be based on the morphology information from the electrograms from different atrial and ventricular channels. In embodiments, episode adjudication for detecting a trigger event may be performed by any number of different components, and/or combinations of components, of the system 100.

According to embodiments, the management server 114 may be used to analyze information obtained in accordance with a study prescription. In embodiments, the management server 114 may additionally, or alternatively, be configured to detect a trigger event, generate a study prescription, provide reports to user devices 116 and/or mobile devices 118, manage patient information, configure therapy regimens, manage/update device software, and/or the like. In embodiments, the management server 114 may be, include, or be included within a server, a server cluster, a computer system, a cloud platform, an enterprise network, and/or the like. Additionally, although illustrated as a device, the management server 114 may, in embodiments, be implemented, at least in part, as software instantiated by any number of devices.

The management server 114 may, for example, index information using a database 124. The database 124 may be, or include, one or more tables, one or more relational databases, one or more multi-dimensional data cubes, one or more non-relational databases, and/or the like. Further, though illustrated as a single component, the database 124 may, in fact, be a plurality of databases 124 such as, for instance, a database cluster, which may be implemented on a single computing device or distributed among a number of computing devices, memory components, or the like.

The management server 114 may be configured to perform security functions, verification functions, and/or the like. Due to potential risks associated with inaccurate adjudication of episodes, detection of triggers, and adjustments in therapy provided by medical devices, it may be desirable for aspects of an at least partially automated system 100 to include safeguards such as, for example, verification of calculations, clinician oversight, and/or the like.

For example, before a study prescription is provided to the IMD 102, the management server 114 may provide a notification of the study prescription to a clinician or other user via the user device 116, mobile device 118, and/or the like. The user (e.g., clinician), in response to receiving the notification, may request a description of the study prescription. In embodiments, the notification of the study prescription may include a description thereof, and may include an indication of a longevity impact associated with the study prescription. As is explained in further detail below, a value may be determined that reflects an impact on the longevity of one or more components of the IMD 102 that is likely to result from execution of a particular study prescription. By presenting this longevity impact value to a user, along with a description of the study prescription, the user is provided with an opportunity to allow the study prescription to be executed or to prevent execution thereof, depending on whether the user believes that the impact on the longevity of the device is outweighed by the potential benefits of executing the study prescription. According to embodiments, the system 100 may include a component that performs this analysis in an automated fashion, based on criteria that may be provided by users and/or learned using a machine-learning technique.

The user (or component or automated process) may provide a confirmation (or denial) of the study prescription to the management server 114. In response to receiving the confirmation, the management server 114 may proceed with providing the study prescription to the IMD 102 for execution. In this manner, embodiments facilitate obtaining a confirmation of a study prescription, or aspects thereof, before implementing the study prescription. In embodiments, for example, a study prescription may be provided to the IMD 102 but may not be executable by the IMD 102 until the IMD 102 receives an enablement command from another device such as, for example, the EMD 106, the external communications device 110, the management server 114, and/or the like. The enablement command may be provided upon receiving a confirmation of the study prescription by, for example, a clinician. According to embodiments, the management server 114 may be configured to provide any number of other, or alternative, functions associated with patient management and/or monitoring.

According to various embodiments, the management server 114 includes enough processing power to analyze and process large amounts of data collected from other devices in the system 100 (e.g., the IMD 102 and/or the EMD 106), as well as to process statistics and perform analysis. The management server 114 may also include identification and/or contact information (e.g., IP addresses, MAC addresses, telephone numbers, and/or product serial numbers) for the various devices communicating with it, such as the EMD 106, the external communications device 110, the programmer 112, the user device 116, and/or the mobile device 118. For example, each device 106, 110, 112, 116, and 118 may be assigned a hard-coded or static identifier (e.g., IP address, telephone number, etc.), which allows the management server 114 to identify which device's (or subject's) information the management server 114 is receiving at a given instant. These identifiers may also be used to direct communications to the various devices. In embodiments, each device 106, 110, 112, 116, and 118 may be assigned, by the management server 114, a unique identification number, and/or a unique patient identification number may be transmitted with each transmission of data.

According to embodiments, when a device is first activated, any one or more of several techniques may be used to associate data received by the system 100 with a given subject. For example, each device 106, 110, 112, 116, and 118 may include a unique identification number and a registration form that is filled out by the patient, caregiver, and/or field representative. The registration form may be used to collect the necessary information to associate collected data with the subject. Alternatively, the user can logon to a web site to allow for the registration information to be collected. In another embodiment, a barcode is included on each device 106, 110, 112, 116, and 118 that is scanned prior to or in conjunction deployment of the device 106, 110, 112, 116, and 118 to provide the information necessary to associate the recorded data with the given patient.

In embodiments, the system 100 may be configured so that various components of the system 100 provide reporting to various individuals (e.g., patients and/or clinicians). For example, different levels of reporting may be provided by (1) the EMD 106 and/or the external communications device 110 and (2) the management server 114. The EMD 106 and/or the external communications device 110 may be configured to conduct preliminary analysis of data gathered from the IMD 102, and provide reporting should an acute situation (e.g., an episode such as a trigger event) be detected. For example, if the EMD 106 and/or the external communications device 110 detects that a significant heart arrhythmia is imminent or currently taking place, the EMD 106 and/or the external communications device 110 may provide reporting to the patient in the form of an audible or visual alarm.

In addition to forms of reporting including visual and/or audible information, the system 100 may also communicate with and/or reconfigure one or more of the devices 102, 106, 110, and/or 112. For example, if the IMD 102 is part of a cardiac rhythm management system, the management server 114 may communicate with the device 102 and reconfigure the therapy provided by the cardiac rhythm management system based on the data collected from one or more of the devices 102, 106, 110, and/or 112. In another embodiment, the management server 114 may provide to the EMD 106 and/or the external communications device 110 recorded data, an ideal range for the data, a conclusion based on the recorded data, and/or a recommended course of action. This information may be displayed on the EMD 106 and/or the external communications device 110 for the patient to review or made available for the patient and/or clinician to review.

Any number of various components of the system 100 depicted in FIG. 1 may be communicatively coupled via the networks 120 and/or 122. The networks 120 and/or 122 provide for communications between and among various components of the system 100, such as the devices 102, 106, 110, 112, 114, 116, and/or 118. FIG. 1 illustrates one embodiment for the communication system 100. The networks 120 and/or 122 may be, or include, any number of different types of communication networks such as, for example, a bus network, a short messaging service (SMS), a local area network (LAN), a wireless LAN (WLAN), a wide area network (WAN), the Internet, a P2P network, custom-designed communication or messaging protocols, and/or the like. The networks 120 and/or 122 may include a combination of multiple networks.

A variety of communication methods and protocols may be used to facilitate communication between devices 102, 106, 110, 112, 114, 116, and/or 118. For example, wired and wireless communications methods may be used. Wired communication methods may include, for example and without limitation, traditional copper-line communications such as DSL, broadband technologies such as ISDN and cable modems, and fiber optics, while wireless communications may include cellular, satellite, radio frequency (RF), Infrared, etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used.

The various communications between the components of the system 100 may be made secure using several different techniques. For example, encryption and/or tunneling techniques may be used to protect data transmissions. Alternatively, a priority data exchange format and interface that are kept confidential may also be used. Authentication may be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and verification techniques may also be used to detect and correct data transmission errors.

In embodiments, varying levels of security may be applied to communications depending on the type of information being transmitted. For example, in embodiments, the management server 114 (or other device) may be configured to apply stricter security measures to confidential health care information than to demographic information. Similarly, even more security may be applied to communications of information used for controlling therapy, adjudicating episodes, and/or the like.

Additionally, in embodiments, communications among the various components of the system 100 may be enhanced using compression techniques to allow large amounts of data to be transmitted efficiently. For example, the devices 102, 106, 110, 112, 114, 116, and 118 may compress information prior to transmitting the information to another device. In embodiments, adaptive compression techniques may be employed such as, for example, the techniques disclosed in U.S. Pat. No. 8,849,682, the entirety of which is hereby incorporated by reference herein.

The illustrative patient management and monitoring system 100 shown in FIG. 1 is not intended to suggest any limitation as to the scope of use or functionality of embodiments of the present disclosure. Neither should the illustrative system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
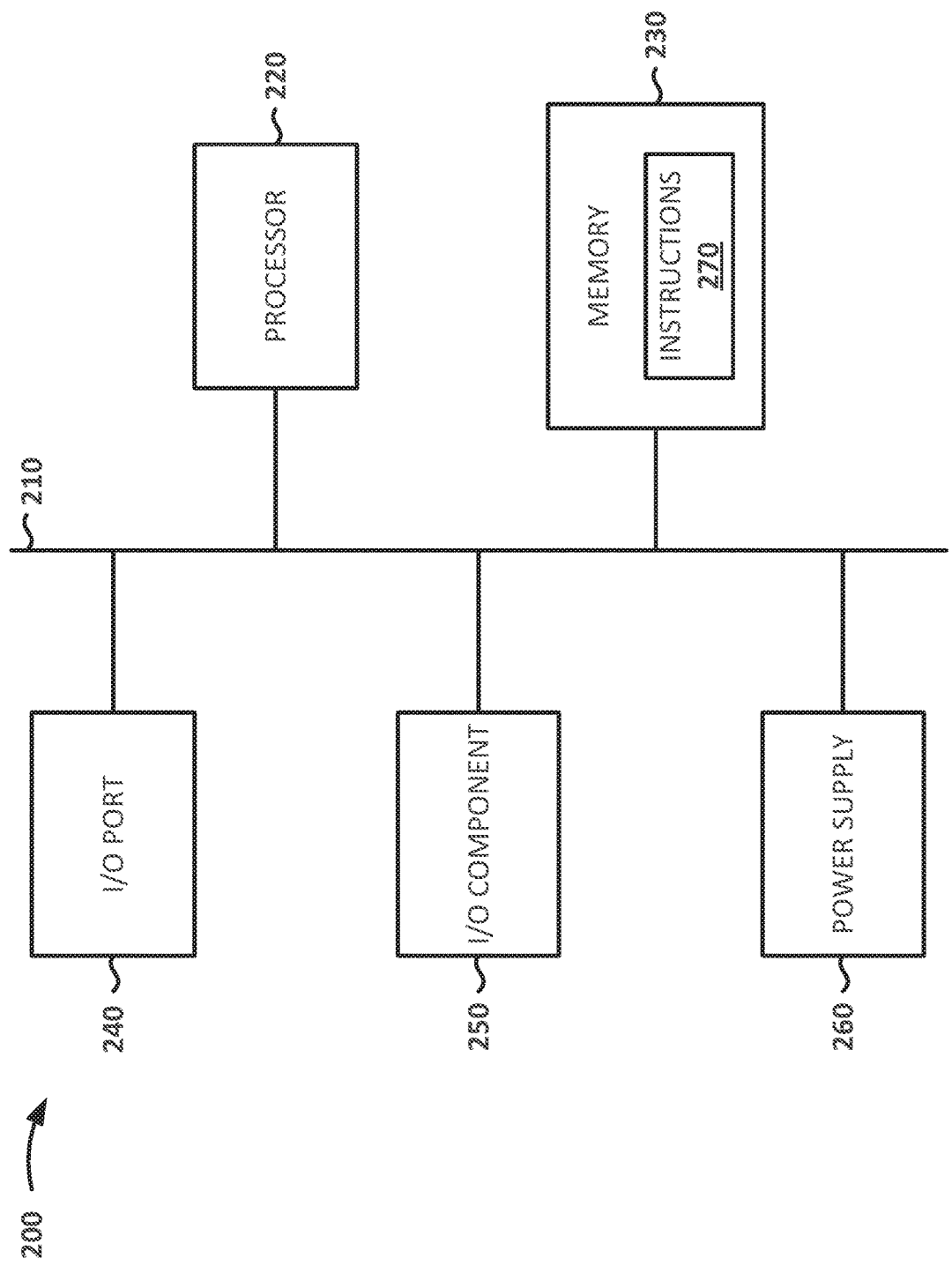
FIG. 2 is a block diagram of an illustrative computing device 200, in accordance with embodiments of the disclosure.

According to various embodiments of the disclosed subject matter, any number of the components depicted in FIG. 1 (e.g., the IMD 102, the EMD 106, the external communication device 110, the programmer 112, the management server 114, the mobile device 116, and/or the user device 118) may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 270 for causing the processor 220 to implement aspects of embodiments of system components discussed herein and/or to perform aspects of embodiments of methods and procedures discussed herein.

The computer-executable instructions 270 may include, for example, computer code, machine-useable instructions, and the like such as, for example, program components capable of being executed by one or more processors 220 associated with the computing device 200. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. Neither should the illustrative computing device 200 be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
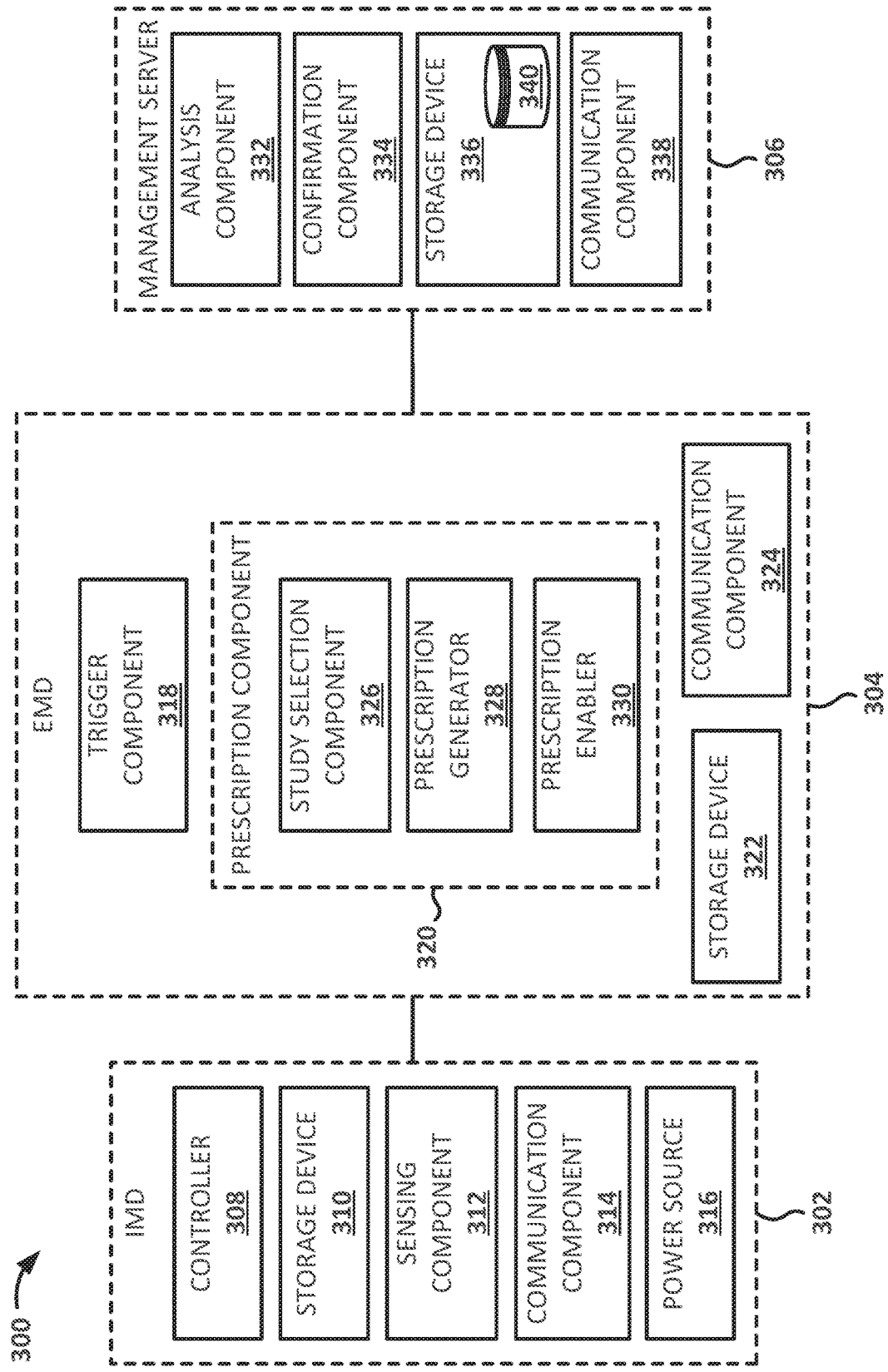
FIG. 3 is a block diagram of an illustrative medical system 300, in accordance with embodiments of the disclosure.

FIG. 3 is a block diagram depicting an illustrative patient monitoring system 300, in accordance with embodiments of the disclosure. As shown, the system 300 includes an IMD 302, an EMD 304, and a management server 306. Embodiments of the system may include more than one IMDs 302, more than one EMDs 304, and more than one management servers 306. The IMD 302 may be, be similar to, include, or be included in, the IMD 102 depicted in FIG. 1; the EMD 304 may be, be similar to, include, or be included in, the EMD 106, programmer 112, the user device 116, the mobile device 118, the user and/or the external communication device 110 depicted in FIG. 1; and the server 306 may be, be similar to, include, or be included in, the server 114 depicted in FIG. 1. The EMD 304 and/or the management server 306 may be, be similar to, include, or be included within the computing device 200 depicted in FIG. 2.

According to embodiments illustrated in FIG. 3, the IMD 302 includes a controller 308, a storage device 310, a sensing component 312, a communication component 314, and a power source 316. The controller 308 may include, for example, a processing unit, a pulse generator, and/or the like. The controller 308 may be any arrangement of electronic circuits, electronic components, processors, program components and/or the like configured to store and/or execute programming instructions, to direct the operation of the other functional components of the IMD 102, to perform arrhythmia detection and/or classification algorithms, to store physiologic data obtained by the sensing component 312, and/or the like, and may be implemented, for example, in the form of any combination of hardware, software, and/or firmware.

In embodiments, the controller 308 may be a programmable micro-controller or microprocessor, and may include one or more programmable logic devices (PLDs) or application specific integrated circuits (ASICs). In some implementations, the controller 308 may include memory as well. Although embodiments of the present system 300 are described in conjunction with an IMD 302 having a microprocessor-based architecture, it will be understood that the IMD 302 (or other device) may be implemented in any logic-based integrated circuit architecture, if desired. The controller 308 may include digital-to-analog (D/A) converters, analog-to-digital (N/D) converters, timers, counters, filters, switches, and/or the like. The controller 308 may execute instructions and perform desired tasks as specified by the instructions.

The controller 308 may also be configured to store information in the storage device 310 and/or access information from the storage device 310. The storage device 310 may be, be similar to, include, or be included within, the storage device 230 depicted in FIG. 2. That is, for example, the storage device 310 may include volatile and/or nonvolatile memory, and may store instructions that, when executed by the controller 308 cause methods and processes to be performed by the IMD 302. In embodiments, the controller 308 may process instructions and/or data stored in the storage device 312 to control delivery of an electrical stimulation therapy by the IMD 302, to control sensing operations performed by the IMD 302, to control communications performed by the IMD 302, and/or the like.

The IMD 302 may sense physiological parameters using a sensing component 312 that may include, for example, one or more electrodes (not shown), one or more sensors (not shown), or a combination of these. In embodiments, the sensing component 312 may include any number of electrical circuits, electronic components, processors, program components and/or the like. The storage device 310 may be used to store sensed information according to some implementations. Information from sense circuits included in the sensing component 312 may be used to adjust therapy, sensing, and/or communications parameters.

In embodiments, the sensing component 312 may be configured to sense intrinsic cardiac electrical signals in a manner similar to known electrocardiogram (ECG) electrodes, which signals are transmitted via conventional techniques to the controller 308. In various embodiments, the sensing component 312 may be configured to sense other patient physiologic or environmental parameters in addition to, or alternative to, cardiac signals. In embodiments, the sensing component 312 may include temperature sensors (e.g., thermocouples or thermistors), barometers, acoustic sensors, pressure sensors, optical sensors, motion or impact sensors (e.g., accelerometers, inertial measuring units (IMUs)), strain sensors, Doppler systems, ultrasound sensors, and/or the like, in any number of various types of configurations. The foregoing sensors allow the IMD 302 to be capable of sensing and recording physiologic parameters such as, for example, patient movement, posture, respiratory cycles, heart sounds, and/or the like. The output from the sensing component 312 may be used in arrhythmia detection and classification, therapy selection, trigger event detection, study prescription performance, and/or the like.

The communication component 314 may include, for example, circuits, program components, and one or more transmitters and/or receivers for communicating wirelessly with one or more other devices such as, for example, the EMD 304. According to various embodiments, the communication component 314 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 314 may include any combination of hardware, software, and/or firmware configured to facilitate establishing, maintaining, and using any number of communication links. In embodiments, the communication component 314 of the IMD 302 facilitates wireless communication with the EMD 304, which may include an external device (e.g., the EMD 106 depicted in FIG. 1, the external communication device 110 depicted in FIG. 1, and/or the programmer 112 depicted in FIG. 1). In embodiments, the communication component 314 may also facilitate communications with other IMDs such as, for example, to facilitate coordinated operations between the IMDs.

In other embodiments, other forms of wireless telemetry may be utilized for communications. For example, in embodiments, other RF telemetry technologies may be employed. Alternatively, and/or additionally, inductive telemetry, acoustic telemetry and/or the like may be employed for communicating with, e.g., the EMD 304. In embodiments, conductive telemetry may be employed, in which case, for example, the communication component 314 may interact with one or more sensing/therapy electrode(s) to transmit and/or receive communications encoded in electrical pulses.

The power source 316 provides electrical power to the other operative components (e.g., the controller 308, the sensing component 310, the storage device 312, and the communication component 314), and may be any type of power source suitable for providing the desired performance and/or longevity requirements of the IMD 102. In various embodiments, the power source 316 may include one or more batteries, which may be rechargeable (e.g., using an external energy source). The power source 316 may include one or more capacitors, energy conversion mechanisms, and/or the like. Power sources for medical devices such as the IMD 102 are well known, and are therefore not discussed in greater detail herein.

As shown in FIG. 3, the EMD 304 includes a trigger component 318, a prescription component 320, a storage device 322, and a communication component 324. In embodiments, the trigger component 318 and the prescription component 320 may be implemented in any combination of hardware, software, and/or firmware, and may be implemented, at least in part, by a controller (not shown) that may be identical to, or similar to, the controller 308 of the IMD 302. Additionally, the storage device 322 and communication component 324 may be identical to, or similar to, the storage device 310 and the communication component 314, respectively, of the IMD 302. The EMD 304 may include any number of other components or combination of components including, for example, a sensing component, a therapy component, and/or the like.

The trigger component 318 is configured to detect a trigger event. According to embodiments, the trigger component 318 may be configured to implement any number of different adjudication algorithms to detect a trigger event. The trigger component 318 may detect a trigger event based on information received from any number of other components, devices, and/or the like. For example, the trigger component 318 may obtain physiological parameter information from the IMD 302 (via a communication between the communication component 314 and the communication component 324) and may use that physiological parameter information to detect a trigger event. Trigger events may be user defined, system defined, statically defined, dynamically defined, and/or the like. The trigger component 318 may reference trigger criteria stored in memory (e.g., the storage device 322) to determine whether a trigger event has occurred. The trigger criteria may be established by a clinician, a patient, an algorithm, and/or the like.

For example, in embodiments, the trigger component 318 may reference a first set of trigger criteria for determining whether a first trigger event has occurred, a second set of trigger criteria for determining whether a second trigger event has occurred, and/or the like. The first trigger event may be, for example, a tachyarrhythmia episode (e.g., an occurrence of an abnormally fast heart rate). Because different patients may have different average heart rates and heart rate characteristics, the trigger criteria for detecting an increased heart rate as a trigger event may be different for a first patient than it is for a second patient.

Additionally, in the context of a single patient, an increased heart rate may be more or less concerning depending on the situation. For example, to detect a trigger event based on an increased heart rate, the trigger component 318 may also be configured to obtain information from a position sensor (e.g., an accelerometer), a motion sensor, a respiration sensor (e.g., a minute volume component implemented in the IMD 302), and/or the like. A set of trigger criteria also may be dynamically adapted over time, using a machine-learning process. That is, for example, as a patient ages, adopts changes to daily routines (e.g., diet, exercise, sleep habits, etc.), and/or the like, the trigger component 318 may dynamically adapt trigger criteria so that, for example, a smaller increase in heart rate may be detected as a trigger event when the patient is older than when the patient was younger. Additionally, machine-learning techniques may be employed to adapt trigger criteria to more rapidly-changing scenarios such as, for example, the impact of adjusting to a new medication, the impact of a temporary adjustment in sleep schedule, the impact of the air quality in a particular location (e.g., outside vs. inside, downtown vs. at home, one city vs. another, etc.), the impact of an allergic reaction to an environmental stimulus, the impact of a psychological response to an increase or decrease in an amount of sunlight over the course of one or more days, the impact of a rapid change in barometric pressure, and/or the like. According to embodiments, adapting a set of trigger criteria may include adjusting one or more thresholds, adjusting one or more value ranges, adding or subtracting types of information to be considered (e.g., requiring additional, or fewer, inputs to an adjudication algorithm), adjusting weight applied to one or more inputs, adjusting error terms, adjusting boundary conditions, and/or the like.

Upon detecting a trigger event, the trigger component 318 may be configured to notify the prescription component 320, which generates and/or enables a study prescription. In embodiments, the prescription component 320 may be configured to generate and/or enable a study prescription in response to any number of other occurrences as well as, or in lieu of, receiving notification of a trigger event. For example, the prescription component 320 may be configured to generate and/or enable a study prescription in response to receiving user input, a change in state of one or more system variables, and/or the like.

As described above, the study prescription may be a set of executable instructions that, when executed by one or more components of the system 300, facilitate performing a study, in which certain parameter values are obtained, stored, and/or analyzed. For example, although an IMD may be obtaining data continuously, or continually, a study prescription may be configured to cause the IMD to store particular types of data for a subsequent batch dump. In embodiments, the study prescription may include a communication scheme that facilitates providing information from the IMD 302 to the EMD 304, while mitigating impact on the longevity of the IMD 302, or any component thereof. That is, for example, a study prescription may be configured to facilitate an information transfer from the IMD 302 that results in a useful amount of information being transferred to the EMD 304 (e.g., such that an adjudication algorithm may be able to reach a conclusion within a certain confidence range) while seeking to mitigate impact on the life of the power source 316, communication component 314, and/or any other aspect of the IMD 302. Operations may impact the longevity of the IMD 302, and/or various components thereof, in any number of ways including, for example, by depleting a power source, by causing wear in a structure, and/or the like.

The communication scheme may be designed based on device parameter information, physiological parameter information, and/or the like. For example, the prescription component 320 may determine that, to evaluate a particular situation with a particular amount of confidence, the appropriate adjudication algorithm or algorithms would require a certain minimum information input, which would have the least impact on the longevity of the IMD 302 if the information were obtained by the sensors according to a particular scheme, was batched according to a particular scheme, and was communicated to the EMD 304, in batches, according to a particular scheme.

As shown in FIG. 3, the prescription component 320 may include a study selection component 326 that is configured to select a particular study to be performed. In the case of a study that is to be performed for the purpose of diagnosis, for example, the study selection component 326 may be configured to select a diagnostic model. In the case of a study that is to be performed for the purpose of therapy adjustment, the study selection component 326 may be configured to select a therapy model; and in the case of a study that is to be performed for the purpose of evaluating device performance, the prescription component 320 may be configured to select a device model. In embodiments, the prescription component 320 may be configured to identify a study paradigm (e.g., to determine the type of study or information sought in the study that is to be performed), and, based on the study paradigm, identify one or more candidate models. The study paradigm may be determined based on user input, historical information, machine-learning techniques, requests for information, and/or the like.

Within a study paradigm, the study selection component 326 may be configured to identify one or more candidate models based on trigger event information, user input, device input, and/or the like. For example, based on trigger event information, the study selection component 326 may be configured to identify a set of candidate models, each of which may be capable of producing an output that would provide additional information to assist in characterizing the trigger event, characterizing a situation that may be associated with the trigger event (e.g., a condition of which the trigger event is a symptom), facilitating therapy adjustment, and/or the like. Each candidate model may include a set of inputs, a set of algorithms, and/or a set of outputs, some of which may be required, while others may be optional. Each set of inputs, algorithms, and/or outputs may also include various parameters, limitations, requirements, and/or the like. The study selection component 326 may determine a cost associated with each input, algorithm, output, or combination thereof. The cost may refer to an impact on the longevity of the IMD 302 associated with the particular input, algorithm, output, or combination.

For example, a cost associated with an input may be a value that reflects an impact on the power source 316 (e.g., an indication of how much of the life of the power source 316 will be consumed) by obtaining, at the EMD 304, the information specified by the input. Thus, for example, the cost associated with an input may be determined based on power consumption associated with operating the sensing component 312 to sense information to be provided as the input, power consumption associated with processing, using the controller 308, sensed information to obtain derived information to be provided as the input, power consumption associated with storing aspects of the input information in the storage device 310, and power consumption associated with transmitting, using the communication component 314, the input information to the EMD 304. The cost may also depend on any number of various parameters and/or criteria associated with sensing (e.g., sampling rate, resolution, the particular sensor used, sensing thresholds etc.), processing (e.g., sampling rate, resolution, aggregation, etc.), storing, and/or transmitting (e.g., whether the transmission is streaming, batched, RF, inductive, etc.).

Based on the costs associated with candidate models, as well as any number of other considerations (e.g., user preferences, patient status, etc.), the study selection component 326 selects a study to be used and the prescription generator 328 generates the prescription for that study. In doing so, the prescription generator 328 may configure any number of different aspects of the study based on considerations similar to those described above used in selecting the study. For example, the prescription generator 328 may determine a resolution threshold (that is, a minimum data resolution that will provide enough information for the study to produce an output or an output of a certain quality). Additionally, the prescription generator 328 may also determine costs associated with various inputs, algorithms, outputs, and/or the like, of the study. In embodiments, the study selection component 326 may provide resolution threshold and/or cost information to the prescription generator 328.

For example, for a required input, the study selection component 326 may determine ranges of parameters associated with that input. That is, for example, a selected diagnostic model may require at least five blood pressure readings to be obtained over the course of a minute. The study selection component 326 may determine, based on device parameter information (that may be received from an IMD, a server, and/or the like), a cost associated with obtaining five blood pressure readings within a minute and may, in embodiments, identify alternative parameters associated with the input. That is, for example, the study selection component 326 may determine that the selected study may still be effective in diagnosing the patient's condition, within a certain range of confidence, if, instead of obtaining five blood pressure readings in a minute, the IMD 302 were to obtain 10 blood pressure readings over the course of three minutes. Similarly, the study selection component 326 may determine that, instead of transmitting a set of data in a streaming fashion over the course of five minutes using RF telemetry, the IMD could preserve longevity by transmitting the set of data in ten different batches, over the course of ten minutes, using inductive communications. According to embodiments, the study selection component 326 may determine any number of different costs associated with any combination of possible operations, situations, conditions, and/or the like.

Based on the cost information, resolution thresholds, and/or the like, the prescription generator 328 may generate the study prescription. Generating the study prescription may include creating executable instructions, generating object models, formulating a communication scheme, defining sensing, analysis, and/or communication criteria, establishing security parameters (e.g., encryption, etc.), and/or the like.

The prescription enabler 330 may be configured to enable the prescription study to be implemented. For example, in a case where a study prescription is already established, the prescription enabler 330 may be configured to provide an instruction to implement the study, change a status bit, call a function, and/or the like. In embodiments, the prescription enabler 330 also may be configured to work with a confirmation component (e.g., the confirmation component 334 depicted as a component of the management server 306) to obtain confirmation of the study prescription, implement instructions to modify the study prescription, and/or the like.

The management server 306 includes an analysis component 332, a confirmation component 334, a storage device 336, and a communication component 338. In embodiments, the analysis component 332 and the confirmation component 334 may be implemented in any combination of hardware, software, and/or firmware, and may be implemented, at least in part, by a controller, a processor, and/or the like (not shown). The management server 306 may include any number of other components or combination of components including, for example, a security component, a user authorization component, a registration component, a software provisioning component, and/or the like.

In embodiments, the storage device 336 may include a database 340. The database 340 may be, be similar to, include, or be included within the database 120 depicted in FIG. 1. For example, the database 340 may include a number of databases such as, for example, a patient database, a population database, a medical database, a general database, and/or the like. The database 340 may include patient specific data, including data acquired by one or more devices such as, for example, the IMD 302 and/or the EMD 304. The database 340 may include a patient's medical records, historical information, and/or the like. For example, if the IMD 302 is an implantable cardioverter defibrillator (ICD), the database 340 may record device information such as P and R measurements, pacing frequency, pacing thresholds, shocking events, recharge time, lead impedance, battery voltage/remaining life, ATR episode and EGMs, histogram information, and/or other device-specific information. The information stored in the database 340 may be recorded at various times depending on patient requirements, device requirements, study prescriptions, and/or the like.

According to embodiments, the database 340 may include non-patient specific data, such as data relating to other patients and population trends. The database 340 may record epidemic-class device statistics, patient statistics, data relating to staffing by health care providers, environmental data, pharmaceuticals, and/or the like. Embodiments of the database 340 may include clinical data relating to the treatment of diseases, historical trend data for multiple patients in the form of a record of progression of their disease(s) along with markers of key events, and/or the like. The database 340 may include non-medical data related to the patient. In embodiments, the database 340 may include external medical records maintained by a third party, such as drug prescription records maintained by a pharmacy, providing information regarding the type of drugs that have been prescribed for a patient.

In embodiments, the analysis component 332 may utilize information collected by the advanced patient management system 300, as well as information for other relevant sources, to analyze data related to a subject, and provide predictive assessments of the subject's well-being. In performing this analysis, the analysis component 332 may utilize data collected from a variety of sources, include patient specific physiological and subjective data collected by the advanced patient management system 300, medical and historical records (e.g., lab test results, histories of illnesses, etc., drugs currently and previously administered, etc.), as well as information related to population trends provided from sources external to the advanced patient management system 300.

In embodiments, the analysis component 332 may provide a diagnosis of subject health status and predicted trend based on present and recent historical data collected from a device as interpreted by a system of expert knowledge derived from working practices within clinics. For example, the analysis component 332 may perform probabilistic calculations using currently-collected information combined with regularly-collected historical information to predict subject health degradation.

In embodiments, the analysis component 332 may conduct pre-evaluation of the incoming data stream combined with subject historical information and information from subjects with similar disease states. The pre-evaluation system may be based on data derived from working clinical practices and the records of outcomes. The derived data may be processed in a neural network, fuzzy logic system, or equivalent system to reflect the clinical practice. Further, the analysis component 332 may also provide means for periodic processing of present and historical data to yield a multidimensional health state indication along with disease trend prediction, next phase of disease progression co-morbidities, and/or inferences about what other possible diseases may be involved. The analysis component 332 may also integrate data collected from internal and external devices with subjective data to optimize management of overall patient health.

The analysis component 332 may also be configured to analyze data from the IMD 302 and/or the EMD 304 to predict and/or determine device issues and/or failures. For example, if an IMD 302 fails to communicate at an expected time, the analysis component 332 may determine the source of the failure and may cause the management server 306 to take action to restore the performance of the IMD 302, alert a clinician and/or the subject, and/or the like. The analysis component 332 may also perform additional deterministic and probabilistic calculations. For example, the analysis component 332 may be configured to gather data related to charge levels within a given device, such as an ICD, and provide analysis and alerting functions based on this information if, for example, the charge level reaches a point at which replacement of the device and/or battery is necessary. Similarly, early degradation or imminent failure of implanted devices may be identified and proactively addressed, and/or at-risk devices may be closely monitored. In embodiments, one or more of these analyses may be used to dynamically manage execution of a study prescription by the IMD 302 such as, for example, by altering data requests, sampling frequencies, communication schemes, and/or the like.

In one embodiment, the management server 306 may be used as a "data clearinghouse," to gather and integrate data collected from the IMD 302, the EMD 304, and/or other devices (such as, for example, one or more of the devices 102, 106, 110, 112, 116, and 118 depicted in FIG. 1, as well as data from sources outside the advanced patient management system 300. The integrated data may be shared with other interested entities, subject to privacy restrictions, thereby increasing the quality and integration of data available.

In embodiments, the analysis component 332 analyzes the data provided from the various information sources, including the data collected by the advanced patient 300 and external information sources. For example, the analysis component 332 analyzes historical symptoms, diagnoses, and outcomes along with time development of the diseases and co-morbidities. In embodiments, the analysis component 332 may include machine-learning capabilities. For example, the analysis component 332 may be implemented via a neural network (or equivalent) system. The analysis component 332 may be partially trained (i.e., the analysis component 332 may be implemented with a given set of preset values and then learn as the advanced patient management system functions) or untrained (i.e., the analysis component 332 may be initiated with no preset values and must learn from scratch as the advanced patient management system functions). In embodiments, the analysis component 332 may continue to learn and adjust as the advanced patient management system functions (i.e., in real time), or the analysis component 332 may remain at a given level of learning and only advanced to a higher level of understanding when manually allowed to do so.

The analysis component 332 may be configured to use various algorithms and mathematical modeling such as, for example, trend and statistical analysis, data mining, pattern recognition, cluster analysis, neural networks and fuzzy logic. The analysis component 332 may perform deterministic and probabilistic calculations. Deterministic calculations include algorithms for which a clear correlation is known between the data analyzed and a given outcome. For example, there may be a clear correlation between the energy left in a battery of the IMD 302 and the amount of data that can be sensed, processed, and transmitted. Additionally, using the analysis component 332, a bifurcated analysis may be performed for diseases exhibiting similar symptoms. As progressive quantities of data are collected and the understanding of a given disease state advances, disease analysis may be refined such as, for example, where a former singular classification may split into two or more sub-classes.

In addition, patient-specific clinical information may be stored and tracked for hundreds of thousands of individual patients, enabling a first-level electronic clinical analysis of the patient's clinical status and an intelligent estimate of the patient's short-term clinical prognosis. The analysis component 332 may be capable of tracking and forecasting a patient's clinical status with increasing levels of sophistication by measuring a number of interacting co-morbidities, all of which may serve individually or collectively to degrade the patient's health. This may enable the management server 306, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as MI and stroke.

In embodiments, the communication component 338 may be configured to coordinate delivery of feedback based on analysis performed by the analysis component 332. For example, in response to the analysis component 332, the communication component 338 may manage the IMD 302 and/or EMD 304, perform diagnostic data recovery, program the devices, and/or otherwise deliver information as needed. In embodiments, the communication component 338 can manage a web interface that can be accessed by patients and/or caregivers. The information gathered by an implanted device may be periodically transmitted to a web site that is securely accessible to the caregiver and/or patient in a timely manner. In embodiments, a patient accesses detailed health information with diagnostic recommendations based upon analysis algorithms derived from leading health care institutions.

The illustrative patient monitoring system 300 shown in FIG. 3 is not intended to suggest any limitation as to the scope of use or functionality of embodiments of the present disclosure. Neither should the illustrative patient monitoring system 300 be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure. For example, the confirmation component 338 may be integrated with the prescription component 320. As another example, the trigger component 318 may be integrated with the analysis component 332.

Figure 4:
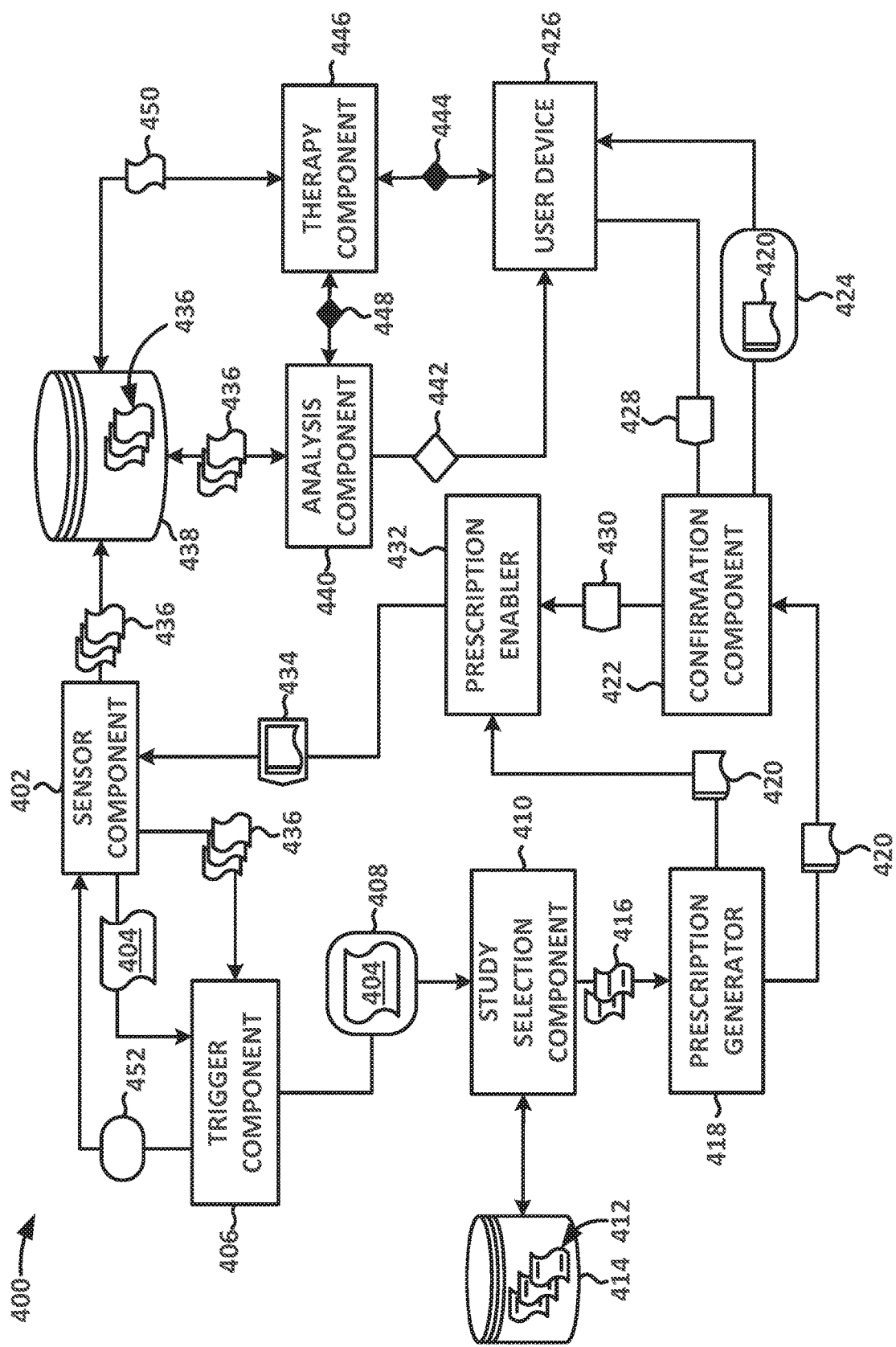
FIG. 4 is a schematic block diagram of an illustrative process 400 for monitoring a patient, in accordance with embodiments of the disclosure.

As described above, any number of various combinations of components depicted in FIG. 3 may be implemented in any number of different ways, on any number of different devices, and/or the like. FIG. 4 is a schematic diagram depicting an illustrative process flow 400 for patient monitoring, in accordance with embodiments of the disclosure. Because any number of the various components depicted in FIG. 4 may be implemented in any number of different combinations of devices, FIG. 4 is depicted, and described, without regard to the particular device(s) within which each component is implemented, but is rather discussed in the context of system components and their functions.

As shown in FIG. 4, a sensing component 402 obtains a set 404 of values of one or more physiological parameters and provides that set 404 of values to a trigger component 406. In embodiments, the sensing component 402 may be, be similar to, include, or be included in, the sensing component 312 depicted in FIG. 3, and may be implemented, for example, in an IMD (e.g., the IMD 102 depicted in FIG. 1 and/or the IMD 302 depicted in FIG. 3) and/or an EMD (e.g., the EMD 106, the external communication device 110, the programmer 112, or the mobile device 118 depicted in FIG. 1; and/or the EMD 304 depicted in FIG. 3). The trigger component 406 may be, be similar to, include, or be included in, the trigger component 318 depicted in FIG. 3, and may also, or alternatively, be implemented in an IMD, an EMD, and/or a server (e.g., the management server 114 depicted in FIG. 1 and/or the management server 306 depicted in FIG. 3). According to embodiments, the set 404 of values may include values of any number of different types of physiological parameters such as, for example, one or more cardiac electrical signals, heart sounds, heart rate, blood pressure measurements, oxygen saturations, and/or the like.

The trigger component 406 analyzes the set 404 of values of the one or more physiological parameters and may detect a trigger event. The trigger component 406 may be configured to provide a notification 408 of the detected event to a study selection component 410. In embodiments, the trigger event may include any number of different types of events, conditions, and/or the like. For example, the trigger event may be an occurrence of an arrhythmia, a sleep apnea event, a snoring event, and/or the like. The trigger event may be a certain value of a parameter, a value of a parameter falling within a certain range, a value of a parameter that exceeds a certain threshold, a combination of certain values of one or more parameters, a combination of one or more values of one or more parameters within a certain range or ranges, a combination of one or more values of one or more parameters that exceed one or more thresholds, and/or any number of different combinations of the foregoing. For example, in embodiments, the trigger event may be an occurrence of a heart rate exceeding a certain threshold at or about the same time that a respiration rate exceeds a certain threshold.

The study selection component 410 may be, be similar to, include, or be included in, the study selection component 326 depicted in FIG. 3, and may also, or alternatively, be implemented in an IMD, an EMD, and/or a server. According to embodiments, the study selection component 410 may, in response to receiving the notification 408 of the trigger event, request information from the trigger component 406, the sensor component 402, and/or the like. For example, in embodiments, the study selection component 410 may request device parameters, physiological parameters, patient demographic parameters, and/or the like. In embodiments, the trigger component 406 may provide information to the study selection component 410 in response to receiving the request from the study selection component 410. In embodiments, the trigger component 406 may provide information to the study selection component 410 even absent a request from the study selection component 410. For example, as shown in FIG. 4, the notification 408 may include the set 404 of values of the one or more physiological parameters that led to detection of the trigger event.

The study selection component 410 may be configured to identify one or more candidate diagnostic models 412, which may be stored, for example, in a database 414. According to embodiments, the candidate diagnostic models 412 may include any number of different types of relationships between information and diagnoses. For example, the candidate diagnostic models 412 may include arrhythmia adjudication algorithms, dynamic statistical models, classifiers, neural networks, and/or the like. In embodiments, each of the candidate diagnostic models 412 includes at least one or more inputs, one or more calculations or relations, and one or more outputs.

The study selection component 410 may be configured to determine input options for each of the identified candidate diagnostic models 412. For example, the study selection component 410 may, for a candidate diagnostic model 412, determine which inputs are required and which inputs are optional, the types of information that may be used as inputs, the amount of information necessary for each input, and/or the like. In embodiments, the study selection component 410 may be configured to determine costs associated with each input option for a particular candidate diagnostic model 412. A cost associated with an input option may be, for example, an amount of processing power, an amount of electrical power consumption, an amount of reduction of the functional life of a device or component, and/or the like.

The cost associated with the input option may be determined based on any number of various parameters such as, for example, device parameters, physiological parameters, and/or the like. In embodiments, for example, a cost associated with an input option may be determined by calculating an amount of power consumption necessary for a sensor component (e.g., the sensor component 402 depicted in FIG. 4) to obtain a set of values of a physiological parameter, an amount of power consumption necessary for a communication component (e.g., the communication component 314 depicted in FIG. 3) to communicate the set of values or other values derived therefrom to another communication component (e.g., the communication component 324 depicted in FIG. 3), an amount of power consumption necessary for an analysis component (e.g., the analysis component 332 depicted in FIG. 3) to perform calculations associated with the particular candidate diagnostic model and using the particular input option, and/or the like.

According to embodiments, the study selection component 410 may select a diagnostic model based, for example, on one or more costs, input options, and/or the like. For example, the study selection component 410 may be configured to select a diagnostic model by identifying a balance between costs (e.g., processing power, transmission power, device longevity) and usefulness. Additionally, in embodiments, the study selection component 410 may select, for the selected diagnostic model, one or more input options, one or more input parameters, one or more output options, and/or the like. For example, as described above, with regard to FIG. 3, the study selection component 410 may determine, for a given diagnostic model, which inputs defined by the model are required and which inputs are optional, costs associated with those inputs, and input parameter options that may be used to reduce total costs of performing the associated study.

The study selection component 410 provides the selected diagnostic model 416, along with the selected inputs, input parameters, outputs, and/or the like, to a prescription generator 418, which may be configured to generate a study prescription 420 and provide the study prescription 420 to a confirmation component 422. According to embodiments, the prescription generator 418 may be, be similar to, include, or be included in, the prescription generator 328 depicted in FIG. 3, and may also, or alternatively, be implemented in an IMD, an EMD, and/or a server. In embodiments, the study prescription 420 may be, include, or be included in, a set of computer-executable instructions.

As shown in FIG. 4, the confirmation component 422 may be, be similar to, include, or be included in, the confirmation component 334 depicted in FIG. 3, and may also, or alternatively, be implemented in an IMD, an EMD, and/or a server. The confirmation component 422 may be configured to provide a prescription notification 424 to a user device 426. As shown in FIG. 4, the prescription notification 424 may include the study prescription 420 and/or information associated therewith. In embodiments, the user device 426 may be the user device 116 depicted in FIG. 1, the mobile device 118 depicted in FIG. 1, and/or the like. The user device 426 may be configured to present the study prescription 420, information about the study prescription, and/or the like, to a user, who may review the information to determine whether the study prescription 420 should be performed. The user device 426 may be configured to receive user input indicating that the study prescription 420 should be confirmed (e.g., that is, an approval of the study prescription 420), rejected, and/or modified. In embodiments, for example, the user device 426 may provide a user interface that includes selectable options for responding to the prescription notification 424, and may include further selectable options or other user interface features configured for allowing a user to configure modifications to the study prescription 420.

The user device 426 may be configured to provide a confirmation response 428 to the confirmation component 422. In response to receiving the confirmation response 428, the confirmation component 422 may be configured to provide a confirmation notification 430 to a prescription enabler 432. The prescription enabler 432 may be, be similar to, include, or be included in, the prescription enabler 330 depicted in FIG. 3, and may also, or alternatively, be implemented in an IMD, an EMD, and/or a server. The prescription generator 418 may also be configured to provide the study prescription 420 to the prescription enabler 432.

In embodiments, the confirmation response 428 may be, or include, one or more modifications (or instructions to make modifications) to the study prescription 420. The modifications may be provided to the prescriptions generator 418, which may make the modifications to the study prescription 420 and provide the modified study prescription to the confirmation component 422 for confirmation, or to the prescription enabler 432. In embodiments, the system may not include a confirmation process, in which case the prescription generator 418 may provide the study prescription 420 directly to the prescription enabler 420.

The prescription enabler 432 may be configured to generate an enabled study prescription 434 in any number of different manners. For example, in embodiments, a study prescription 420 may include pseudocode, a representative model, uncompiled code, and/or the like, in which case, the prescription enabler 432 may be configured to generate executable code, may be configured to compile code, and/or the like. In embodiments, the study prescription 420 may include executable code but may include a status bit that needs to be set in order for the study prescription 420 to be executed, in which case, the prescription enabler 432 may generate the enabled study prescription 434 by setting the status bit. In embodiments, the study prescription 420 may be already stored on an IMD, EMD, and/or the like (e.g., the study prescription may be configured before detection of the trigger event), in which case the enabled study prescription 434 may include an instruction to execute the existing study prescription. In embodiments, the enabled study prescription 434 may include a number of parameters, and/or other information that may be used in performing the study. In embodiments, the study prescription 420 may be, or include, a particular communication scheme by which, for example, an IMD is to communicate information to an EMD. In these cases, the enabled study prescription 434 may be an instruction to begin that communication, enable a particular transceiver, receiver, transmitter, and/or the like, and/or any communication designed to facilitate implementation of the communication scheme.

The prescription enabler 432 may provide the enabled study prescription 434 to the sensor component 402 to be performed. The sensor component 402 may obtain information 436 in accordance with the enabled study prescription 434 and store that information 436 in a storage device 438. In embodiments, the storage device 438 may be, be similar to, include, or be included in, the database 124 depicted in FIG. 1, the memory 230 depicted in FIG. 2, the storage device 310 depicted in FIG. 3, the storage device 322 depicted in FIG. 3, and/or the storage device 336 depicted in FIG. 3, and may also, or alternatively, be implemented in an IMD, an EMD, and/or a server.

An analysis component 440 may access the information 436 and analyze the information 436 to make a determination such as, for example, a diagnosis. The analysis component 440 may be, be similar to, include, or be included in, the analysis component 332 depicted in FIG. 3, and may also, or alternatively, be implemented in an IMD, an EMD, and/or a server. Based on the diagnosis, the analysis component 440 may provide a notification 442 to the user device 426, which may provide a therapy instruction 444 to a therapy component 446. In embodiments, as shown, the analysis component 440 may provide a therapy instruction 448 to the therapy component 446 such as, for example, in response to a determination of a particular diagnosis. The therapy component 446 may store therapy parameter information 450 in the storage device 438, which may be used, for example, by the analysis component 440 in performing the analysis.

Additionally, as shown in FIG. 4, at least a portion of the information 436 obtained during the sensor component's 402 performance of the study may be provided to the trigger component 406, which may provide a dynamic request 452 to the sensor component 402. In embodiments, the dynamic request 452 may include any number of different types of instructions, requests, and/or the like. For example, in embodiments, the trigger component 406 may analyze the information 436 to detect another trigger event and, in response to that other trigger event, instruct the sensor component 402 to modify the enabled study prescription 434, obtain additional information, and/or the like.

The illustrative process flow 400 shown in FIG. 4 is not intended to suggest any limitation as to the scope of use or functionality of embodiments of the present disclosure. Neither should the illustrative process flow 400 be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure. For example, the confirmation component 422 may be integrated with the prescription enabler 432.

Figure 5:
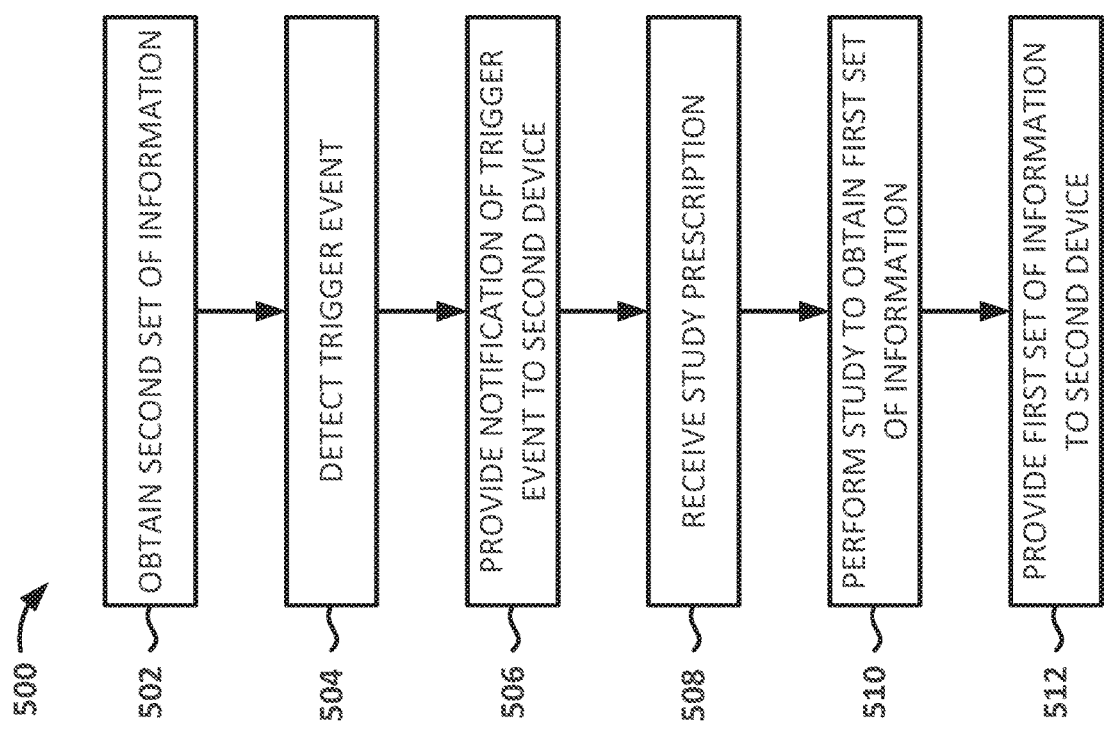
FIG. 5 is a flow diagram depicting an illustrative method 500 of managing communication of values of a first physiological parameter sensed by an implantable medical device (IMD) to an external monitoring device (EMD), in accordance with embodiments of the disclosure.

Embodiments of a patient monitoring system have been described herein, in which study prescriptions are dynamically generated for performing monitoring operations in response to detection of trigger events, and for managing data communications from IMDs. FIG. 5 is a flow diagram depicting an illustrative method 500 of managing communication of values of a first physiological parameter sensed by an implantable medical device (IMD) to an external monitoring device (EMD). Embodiments of the method 500 may be performed by one or more components of a patient monitoring system such as, for example, the patient monitoring system 100 depicted in FIG. 1, the patient monitoring system 300 depicted in FIG. 3, using a process such as, for example, the illustrative process 400 depicted in FIG. 4. In embodiments, for example, the method 500 may be performed by an IMD (e.g., the IMD 102 depicted in FIG. 1 and/or the IMD 302 depicted in FIG. 3).

Embodiments of the illustrative method 500 include obtaining a second set of information (block 502). The second set of information may be obtained by, and/or from, an IMD (e.g., the IMD 102 depicted in FIG. 1 and/or the IMD 302 depicted in FIG. 3), and EMD (e.g., the EMD 106 depicted in FIG. 1, the external communication device 110 depicted in FIG. 1, the programmer 112 depicted in FIG. 1, the user device 116 depicted in FIG. 1, the mobile device 118 depicted in FIG. 1, and/or the EMD 304 depicted in FIG. 3). The second set of information may include any number of different types of information such as, for example, physiological parameter values, device parameter values, patient demographic parameter values, and/or the like. In embodiments, the second set of information includes at least one value of an IMD parameter associated with power consumption. In embodiments, the second set of information includes at least one value of a second physiological parameter.

The method 500 further includes detecting, based on the second set of information, a trigger event (block 504). In embodiments, detecting the trigger event may include evaluating at least a portion of the second set of information to identify one or more occurrences of an event such as, for example, a physiological event, a device event, and/or the like. Examples of trigger events may include, for example, occurrences of snoring, increased heart rate, sleep apnea, increased respiration, and/or the like. Embodiments of the method 500 further include providing a notification of the trigger event to a second device (block 506). The second device may include, for example, the EMD 106 depicted in FIG. 1, the external communication device 110 depicted in FIG. 1, the programmer 112 depicted in FIG. 1, the user device 116 depicted in FIG. 1, the mobile device 118 depicted in FIG. 1, the management server 114 depicted in FIG. 1, the EMD 304 depicted in FIG. 3, and/or the management server 306 depicted in FIG. 3.

In embodiments, the method 500 may include receiving, from the second device and/or a third device, a study prescription (block 508). In embodiments, the first device may generate the study prescription in response to detecting the trigger event. The study prescription may include a communication scheme that is configured based on power consumption associated with information transmission, a set of instructions for performing a monitoring study (e.g., based on a diagnostic model), and/or the like. As shown in FIG. 5, embodiments of the method 500 further include performing the study corresponding to the study prescription to obtain the first set of information (block 510) and providing the first set of information to the second device (block 512). The first set of information may include one or more parameter values of the first physiological parameter, and/or a subset thereof. In embodiments, providing the first set of information to the second device may facilitating transmission, according to the study prescription, of the values of the first physiological parameter from the first device to the second device, and/or otherwise communicating information to the second device in accordance with a specified communication scheme, as described herein.

According to embodiments, the first device (e.g., IMD) may be configured to perform analysis, and the first set of information may be, or include, the results the analysis, and may be provided to the second device. For example, in embodiments, the first device may generate marker data associated with an event (e.g., a detected ventricular fibrillation (VF), a right ventricular sense or premature ventricular contraction (PVC)) and interval data associated with a time between an event and a subsequent event. In embodiments, the first device may provide marker and/or interval information along with values of a first physiological parameter. The first set of information may include physiological parameter values (or other information) combined with, annotated with, modified by, and/or otherwise associated with any number of additional types of information, results of analysis, and/or the like. For example, the first device may transmit, to the second device, an EGM along with markers and interval information. In another embodiment, the first set of information may include a subset of a set of values of a physiological parameter. That is, for example, to reduce the amount of data buffered before a burst transmission, the first device may send an EGM sampled at 200 Hz for 150 ms after a marker and otherwise send the EGM sampled at 20 Hz.

According to embodiments, the study prescription may further include instructions configured to cause the first device to enable one or more sensing components, instructions configured to cause the first device to modify a sampling rate and/or a sample storage rate associated with the one or more sensing components, and/or the like. For example, in embodiments, the study prescription may include instructions configured to cause the first device to enable a first sensing component; to sample, using the first sensing component, a first physiological parameter at a first sampling rate; to store the sampled values of the first physiological parameter at a first sample storage rate; to analyze the stored sampled values to identify a trigger event; and, upon identification of the trigger event, to enable a second sensing component; to sample, using the second sensing component, a second physiological parameter at a second sampling rate (or the first physiological parameter at a second sampling rate); to store the second sampled values of the second physiological parameter (or the first physiological parameter) at a second sample storage rate. The instructions may further be configured to cause the first device to analyze the stored values of the second physiological parameter (or the stored values of the first physiological parameter) and/or to transmit a subset of the stored values to the second device. Any number of different combinations of functions may be performed according to a study prescription.

According to embodiments, the first device may be configured to perform one or more operations before implementing a study prescription. For example, in embodiments, the study prescription may be configured to cause the first device to modify the manner in which its memory is used (during implementation of the study prescription). Prior to enabling the study prescription, the first device may be configured to capture information currently in the memory (or a portion thereof) such as, for example, by dumping the current memory to the second device or another device (e.g., an EMD, an external communication device, a programmer, a server, a mobile device, and/or the like), which may store that information. In embodiments, an option may be provided for clearing the information currently in the memory. The option may be provided to, and responded to by, a user, a process, a device, and/or the like.

Figure 6:
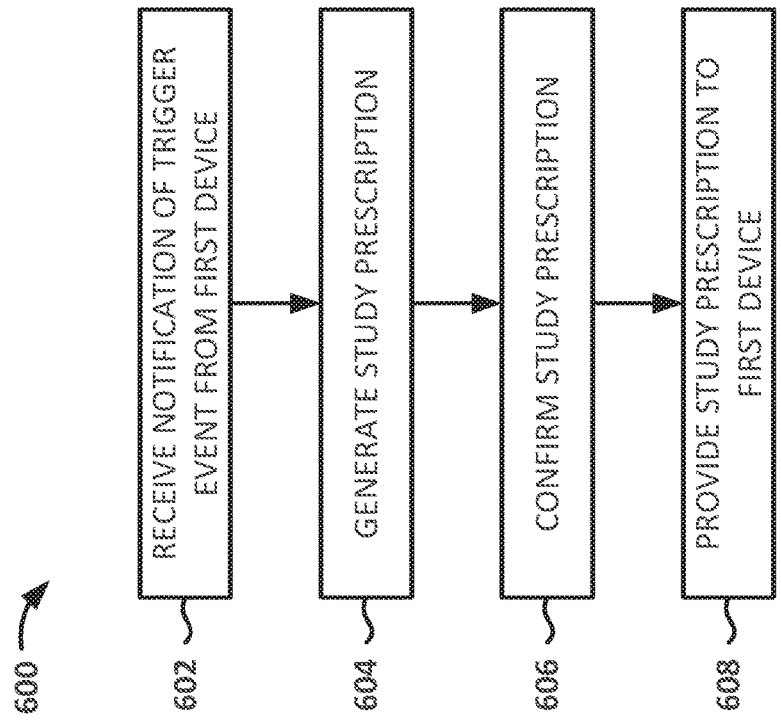
FIG. 6 is a flow diagram depicting an illustrative method 600 of facilitating a monitoring study, in accordance with embodiments of the disclosure.

FIG. 6 is a flow diagram depicting an illustrative method 600 of facilitating a monitoring study in accordance with embodiments of the disclosure. In embodiments, the method 600 may be performed, for example, by a second device, in conjunction with embodiments of the method 500 performed by the first device. As shown in FIG. 6, embodiments of the method 600 may include receiving the notification of the trigger event from the first device (block 602), and, in response to receiving the notification of the trigger event, generating the study prescription (block 604). In embodiments, the method 600 further includes confirming the study prescription (block 606) and providing the study prescription to the first device (block 608).

Figure 7:
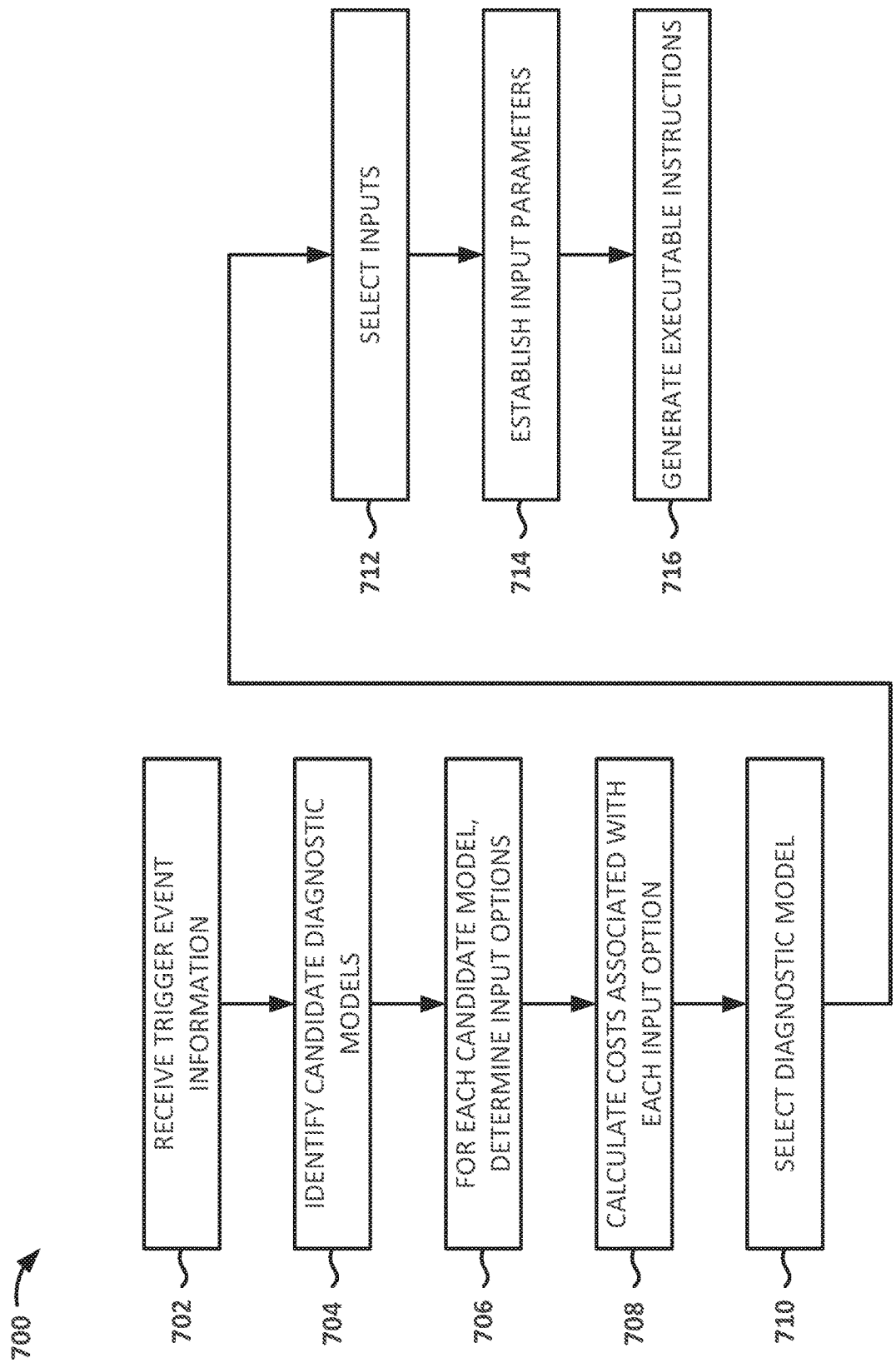
FIG. 7 is a flow diagram depicting an illustrative method 700 of generating a study prescription, in accordance with embodiments of the disclosure.

FIG. 7 is a flow diagram depicting an illustrative method 700 of generating a study prescription in accordance with embodiments of the disclosure. Embodiments of the method 700 may be performed by any one or more components of the patient monitoring system described herein such as, for example, the prescription component 320 depicted in FIG. 3, the prescription generator 328 depicted in FIG. 3, and/or the prescription generator 418 depicted in FIG. 4. Additionally, although the method 700 is described in the context of diagnostic models, it should be understood that aspects of embodiments of the method 700 may be implemented with respect to any number of various types of models including, for example, therapy models, device performance models, and/or the like.

As shown in FIG. 7, embodiments of the method 700 include receiving trigger event information (block 702) and identifying, based on the trigger event information, one or more candidate diagnostic models (block 704). Embodiments of the method 700 further include determining, for each of the candidate diagnostic models, one or more input options (block 706), and calculating, for each of the candidate diagnostic models, a cost associated with each of the one or more input options (block 708). One of the diagnostic models is selected (block 710), based on the calculated cost associated with each of the one or more input options, and a set of inputs for the selected diagnostic model is also selected (block 712). Embodiments of the method 700 further include establishing a set of input parameters associated with the set of inputs (block 714). As shown in FIG. 7, the method 700 may further include generating a set of executable instructions (block 716). The set of instructions may be configured to be executed by an IMD to implement the study prescription.

As discussed above, any number of different components of a patient monitoring system (e.g., the system 100 depicted in FIG. 1) may be utilized for detecting trigger events, performing monitoring studies, and/or the like. Additionally, various communication schemes may be implemented, as part of one or more study prescriptions, for facilitating providing information from an IMD to one or more external devices to facilitate more robust patient monitoring and diagnostic capabilities than those found in the conventional systems involving IMDs. These communication schemes may be implemented by way of any number of different communication flows, one or more of which may be dynamically configurable, between one or more devices. FIGS. 8A, 8B, 8C, 9A, and 9B are schematic flow diagrams depicting illustrative communication flows in accordance with embodiments of the disclosure.

Figure 8A:
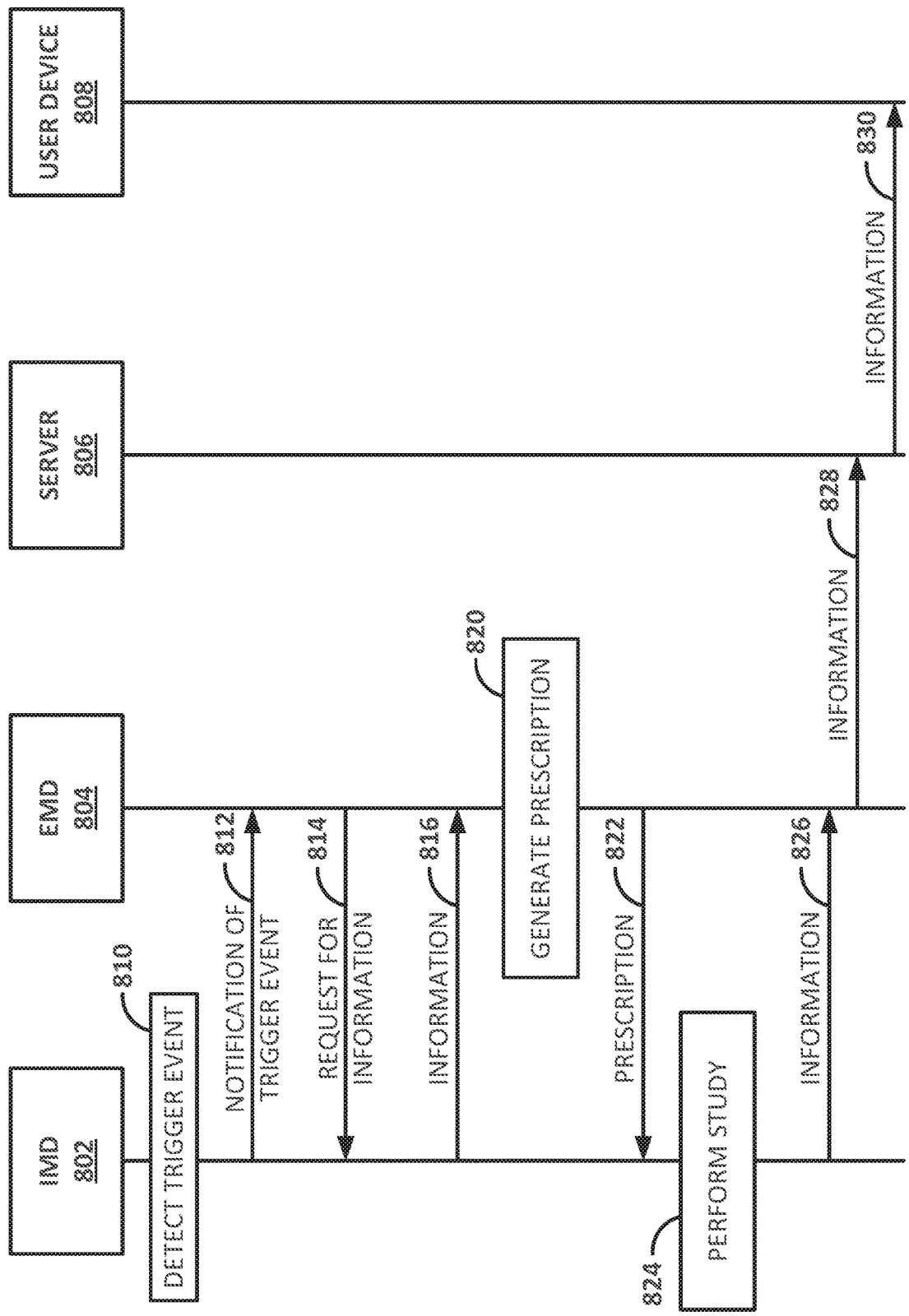
Figure 8B:
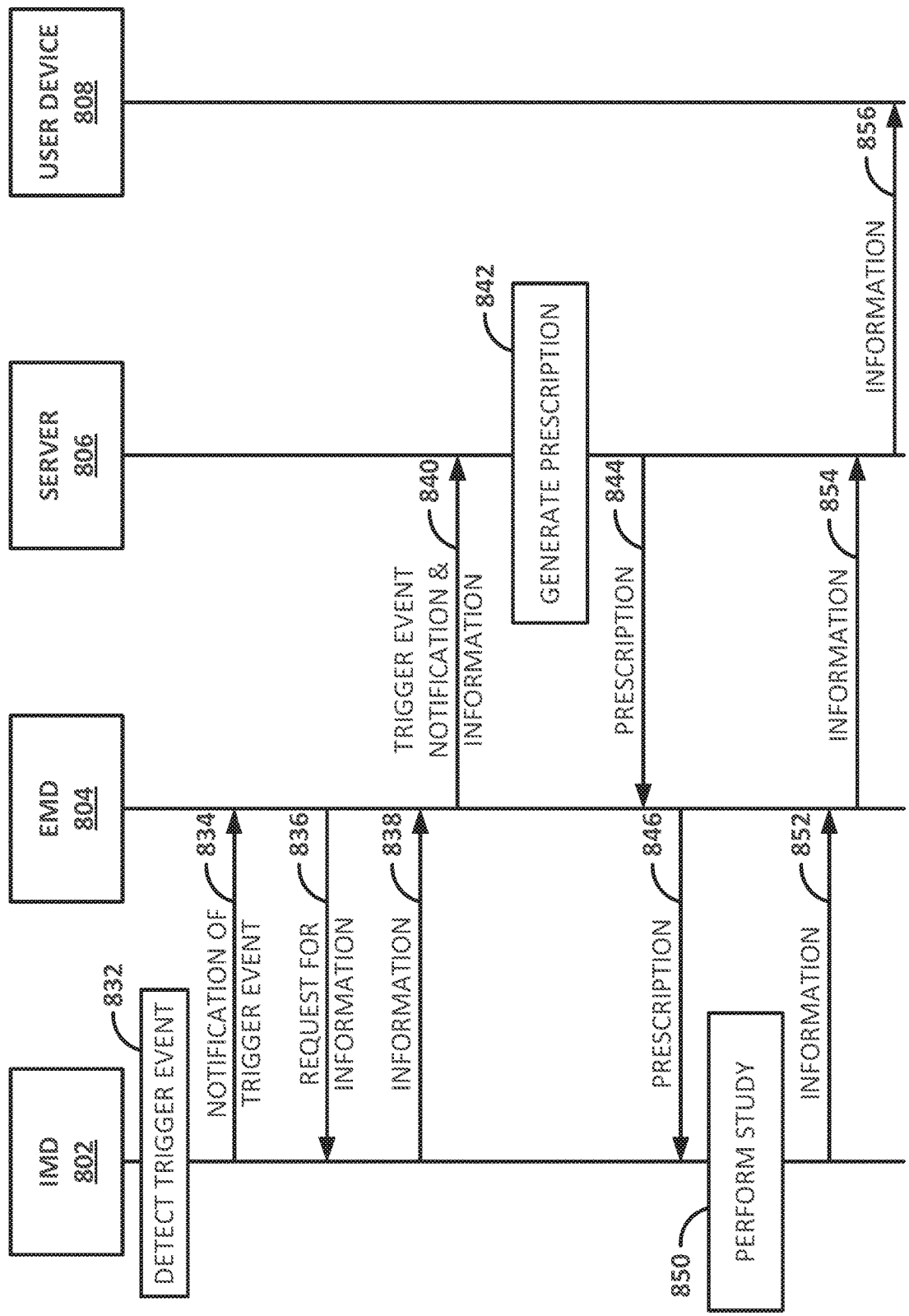

FIGS. 8A, 8B, and 8C depict illustrative communication flows among an IMD 802, an EMD 802, a server 806, and a user device 808. According to embodiments, the IMD 802 may be, be similar to, include, or be included in, any number of different IMDs or systems of IMDs such as, for example, the IMD 102 depicted in FIG. 1, the IMD 302 depicted in FIG. 3, and/or the like. The EMD 802 may be, be similar to, include, or be included in, any number of different external devices or systems of externals devices such as, for example, the EMD 106 depicted in FIG. 1, the external communication device 110 depicted in FIG. 1, the programmer 112 depicted in FIG. 1, the user device 116 depicted in FIG. 1, the mobile device 118 depicted in FIG. 1, the EMD 304 depicted in FIG. 3, and/or the like. Similarly, the server 806 may be, be similar to, include, or be included in, any number of different servers or systems of servers such as, for example, the management server 114 depicted in FIG. 1, the management server 306 depicted in FIG. 3, and/or the like; and the user device 808 may be, be similar to, include, or be included in, any number of different devices or systems of devices such as, for example, the user device 116 depicted in FIG. 1, the mobile device 118 depicted in FIG. 1, the user device 426 depicted in FIG. 4, and/or the like.

In the illustrative communication flow depicted in FIG. 8A, the IMD 802 detects 810 a trigger event and provides 812 a notification of the trigger event to the EMD 804. In response to receiving the notification of the trigger event, the EMD 804 provides 814 a request for information to the IMD 802. For example, in embodiments, the EMD 804 may request physiological parameter values that provide information about the trigger event, device parameter values that provide information about the IMD 802 (e.g., battery life remaining, transmission power parameter values, and/or the like), information about the patient, and/or the like. In response to receiving the request for information 814, the IMD 802 may provide 816, to the EMD 804, the requested information, or a portion thereof. The EMD 804 selects a diagnostic model and generates 820 a study prescription (e.g., based, at least in part, on the information), and provides 822 the study prescription to the IMD 802. The IMD 802 performs 824 the study and provides 826 information obtained as a result of performing the study prescription to the EMD 804. The EMD 804 provides 828 the information (or a portion thereof, or information derived therefrom) to the server 806, which provides 830 the information (or a portion thereof, or information derived therefrom) to the user device 808.

In the illustrative communication flow depicted in FIG. 8B, the IMD detects 832 a trigger event and provides 834 a notification of the trigger event to the EMD 804. In response to receiving the notification of the trigger event, the EMD 804 provides 836 a request for information to the IMD 802. In response to receiving the request for information 814, the IMD 802 may provide 838, to the EMD 804, the requested information, or a portion thereof. The EMD 804 provides 840 the trigger event notification and requested information to the server 806. The server 806 selects a diagnostic model and generates 842 a study prescription, and provides 844 the study prescription to the EMD 804, which provides 846 the study prescription (or a portion thereof, or instructions corresponding thereto) to the IMD 802. The IMD 802 performs 850 the study and provides 852 information obtained as a result of performing the study prescription to the EMD 804. The EMD 804 provides 852 the information (or a portion thereof, or information derived therefrom) to the server 806, which provides 856 the information (or a portion thereof, or information derived therefrom) to the user device 808.

In the illustrative communication flow depicted in FIG. 8C, the IMD provides 858 information to the EMD 804, which uses the information to detect 860 a trigger event. The EMD 804 selects a diagnostic model and generates 862 a study prescription, in response to detecting the trigger event, and provides 864 the study prescription (or a portion thereof, or instructions corresponding thereto) to the IMD 802. The IMD 802 performs 866 the study and provides 868 information obtained as a result of performing the study prescription to the EMD 804. The EMD 804 provides 870 the information (or a portion thereof, or information derived therefrom) to the server 806, which provides 872 the information (or a portion thereof, or information derived therefrom) to the user device 808.

Figure 9A:
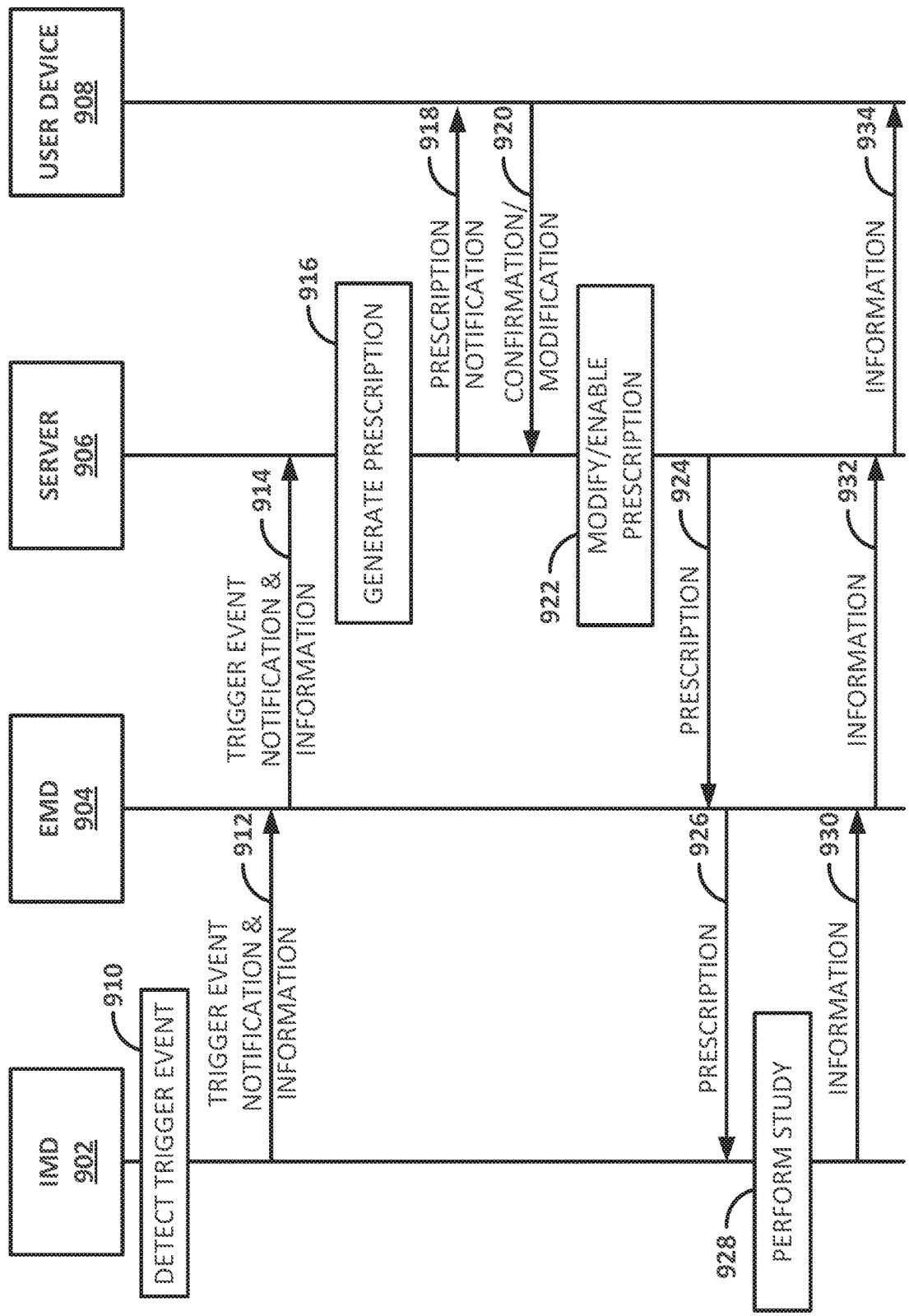
FIGS. 9A and 9B depict illustrative communication flows among an IMD 902, an EMD 902, a server 906, and a user device 908, in which a confirmation process is used to confirm a study prescription, in accordance with embodiments of the disclosure.
Figure 9B:
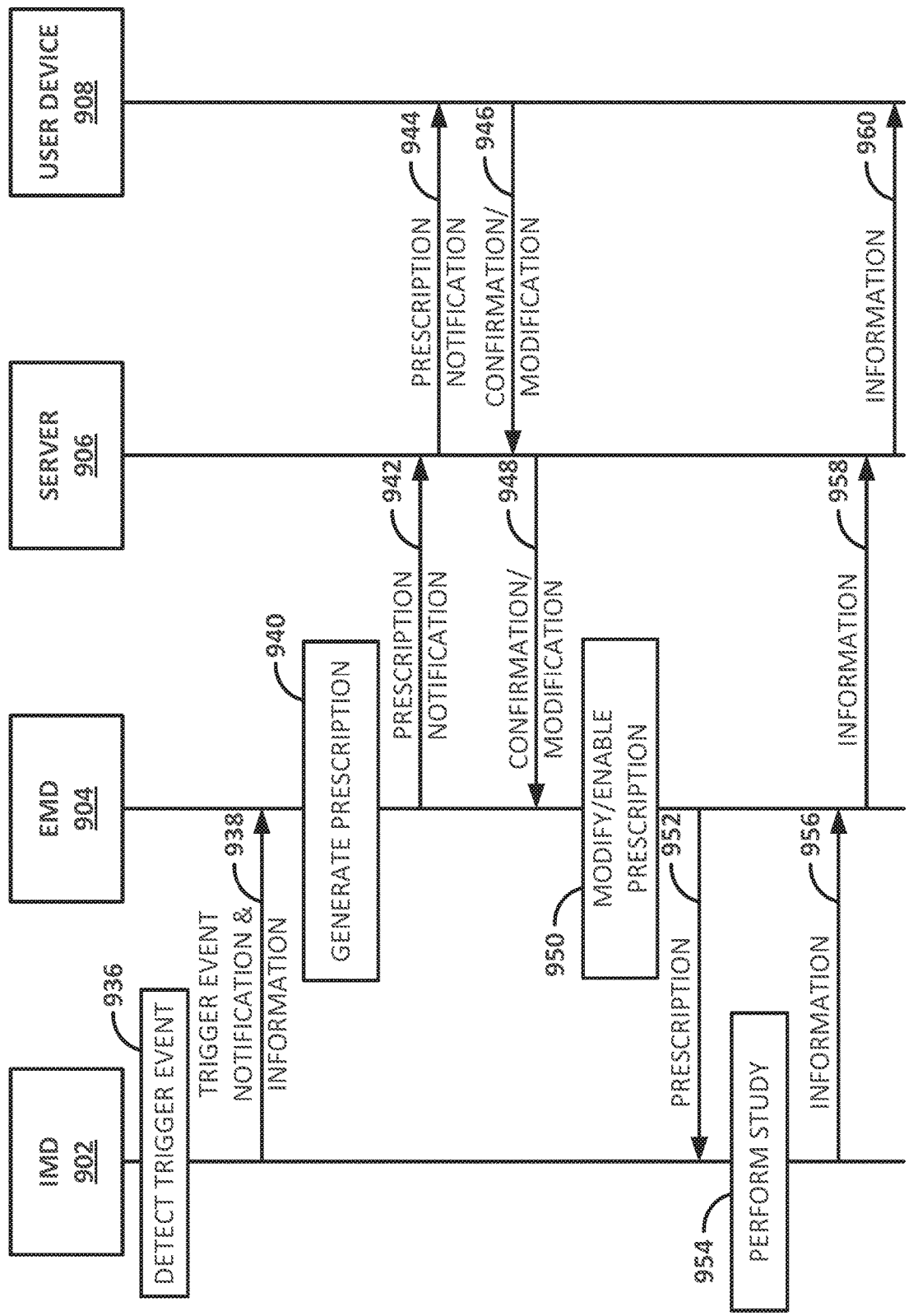

FIGS. 9A and 9B depict illustrative communication flows among an IMD 902, an EMD 902, a server 906, and a user device 908, in which a confirmation process is used to confirm a study prescription, such as, for example, the confirmation process described above in relation to FIG. 4. According to embodiments, the IMD 902 may be, be similar to, include, or be included in, any number of different IMDs or systems of IMDs such as, for example, the IMD 102 depicted in FIG. 1, the IMD 302 depicted in FIG. 3, and/or the like. The EMD 902 may be, be similar to, include, or be included in, any number of different external devices or systems of externals devices such as, for example, the EMD 106 depicted in FIG. 1, the external communication device 110 depicted in FIG. 1, the programmer 112 depicted in FIG. 1, the user device 116 depicted in FIG. 1, the mobile device 118 depicted in FIG. 1, the EMD 304 depicted in FIG. 3, and/or the like. Similarly, the server 906 may be, be similar to, include, or be included in, any number of different servers or systems of servers such as, for example, the management server 114 depicted in FIG. 1, the management server 306 depicted in FIG. 3, and/or the like; and the user device 908 may be, be similar to, include, or be included in, any number of different devices or systems of devices such as, for example, the user device 116 depicted in FIG. 1, the mobile device 118 depicted in FIG. 1, the user device 426 depicted in FIG. 4, and/or the like.

In the illustrative communication flow depicted in FIG. 9A, the IMD 902 detects 910 a trigger event and provides 912 a notification of the trigger event and trigger event information to the EMD 904, which provides 914 the trigger event notification and associated information to the server 906. In response to receiving the notification of the trigger event and associated information, the server 906 selects a diagnostic model and generates 916 a study prescription, and provides 918 a prescription notification to the user device 908. The user device 908 may present the prescription notification or information associated therewith to a user and, in response to receiving user input from the user, provides 920 a confirmation and/or modification of the study prescription to the server 906. In response to receiving the confirmation and/or modification of the study prescription, the server 906 may modify and/or enable 922 the study prescription, and provide 924 the study prescription to the EMD 904, which provides 926 the study prescription (or a portion thereof, or instructions corresponding thereto) to the IMD 902. The IMD 902 performs 928 the study and provides 930 information obtained as a result of performing the study prescription to the EMD 904. The EMD 904 provides 932 the information (or a portion thereof, or information derived therefrom) to the server 906, which provides 934 the information (or a portion thereof, or information derived therefrom) to the user device 908.

In the illustrative communication flow depicted in FIG. 9B, the IMD 902 detects 936 a trigger event and provides 938 a notification of the trigger event and trigger event information to the EMD 904. In response to receiving the notification of the trigger event and associated information, the EMD 904 selects a diagnostic model and generates 940 a study prescription, and provides 942 a prescription notification to the server 906, which provides 944 a prescription notification to the user device 908. The user device 908 may present the prescription notification or information associated therewith to a user and, in response to receiving user input from the user, provides 946 a confirmation and/or modification of the study prescription to the server 906, which provides 948 the confirmation and/or modification to the EMD 904. In response to receiving the confirmation and/or modification of the study prescription, the EMD 904 may modify and/or enable 950 the study prescription, and provide 952 the study prescription (or a portion thereof, or instructions corresponding thereto) to the IMD 902. The IMD 902 performs 954 the study and provides 956 information obtained as a result of performing the study prescription to the EMD 904. The EMD 904 provides 958 the information (or a portion thereof, or information derived therefrom) to the server 906, which provides 960 the information (or a portion thereof, or information derived therefrom) to the user device 908.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system, comprising:
    an implantable medical device (IMD) configured to be implanted within a patient's body,
        the IMD comprising:
            a sensing component configured to obtain values of a first physiological parameter;
            a power source configured to provide power to the IMD; and
            a first communication component configured to transmit, according to a study prescription, the values of the first physiological parameter, the study prescription comprising: (i) a study selection component configured to select a diagnostic model from among a plurality of candidate diagnostic models, (ii) a prescription generator configured to generate the study prescription based on the selected diagnostic model, and (iii) a communication scheme that is configured based on an impact on a longevity of at least one component of the IMD, wherein the communication scheme that is configured based on the impact on the longevity of the at least one component of the IMD corresponds to an amount of power consumption associated with operating the sensing component to obtain the values of the first physiological parameter; and
    an external monitoring device (EMD) configured to be disposed outside of a patient's body, the EMD comprising a second communication component, configured to receive, from the first communication component, the values of the first physiological parameter.

2. The system of claim 1, wherein the communication scheme that is configured based on the impact on the longevity of the at least one component of the IMD further corresponds to an amount of power consumption associated with information transmission from the IMD to the EMD.

3. The system of claim 1, wherein the study prescription further includes instructions configured to cause the sensing component to store the values of the first physiological parameter.

4. The system of claim 1, wherein the communication scheme that is configured based on the impact on the longevity of the at least one component of the IMD further corresponds to storing the values of the first physiological parameter.

5. The system of claim 1, the IMD further comprising a trigger component configured to detect, based on a first set of information, a trigger event, wherein the first set of information comprises a set of values of a second physiological parameter.

6. The system of claim 1, the EMD further comprising a trigger component configured to detect, based on a first set of information, a trigger event, wherein the first set of information comprises values of a second physiological parameter.

7. The system of claim 5, the values of the second physiological parameter comprising additional values of the first physiological parameter.

8. The system of claim 1, further comprising a management server, the management server comprising a third communication component configured to communicate with the second communication component.

9. The system of claim 8, wherein at least one of the EMD and management server provides an analysis component configured to analyze at least the values of the first physiological parameter.

10. The system of claim 9, wherein the analysis component is configured to implement one or more adjudication algorithms to adjudicate a diagnosis based on the values of the first physiological parameter.

11. The system of claim 10, wherein at least one of the IMD, EMD, and management server implements a prescription component, the prescription component configured to enable implementation of the study prescription.

12. The system of claim 8, wherein the management server further comprises a confirmation component configured to provide a notification of the study prescription to a user device, and to receive, from the user device, at least one of a confirmation of the study prescription or a modification of the study prescription.

13. The system of claim 1, the IMD further comprising a controller, wherein the impact on the longevity of the at least one component of the IMD corresponds to an amount of power consumption associated with processing, using the controller, the values of the first physiological parameter.

14. A method comprising:
    sensing values of a first physiological parameter using an implantable medical device (IMD); and
    transmitting, from the IMD to an external medical device (EMD), the values of the first physiological parameter according to a study prescription, the study prescription comprising: (i) a study selection component configured to select a diagnostic model from among a plurality of candidate diagnostic models, (ii) a prescription generator configured to generate the study prescription based on the selected diagnostic model, and (iii) a communication scheme that is configured based on an impact on a longevity of at least one component of the IMD, wherein the communication scheme that is configured based on the impact on the longevity of the at least one component of the IMD corresponds to an amount of power consumption associated with operating the sensing component to obtain the values of the first physiological parameter.

15. The method of claim 14, wherein the communication scheme that is configured based on the impact on the longevity of the at least one component of the IMD further corresponds to an amount of power consumption associated with information transmission from the IMD to the EMD.

16. The method of claim 14, wherein the communication scheme that is configured based on the impact on the longevity of the at least one component of the IMD corresponds to an amount of power consumption associated with processing, using the controller, the values of the first physiological parameter.

17. A system, comprising:
an implantable medical device (IMD) configured to be implanted within a patient's body, the IMD comprising:
a sensing component configured to obtain values of a first physiological parameter;
a power source configured to provide power to the IMD;
a first communication component configured to transmit, according to a study prescription, the values of the first physiological parameter, the study prescription comprising a communication scheme that is configured based on an impact on a longevity of at least one component of the IMD; and
an external monitoring device (EMD) configured to be disposed outside of a patient's body, the EMD comprising a second communication component, configured to receive, from the first communication component, the values of the first physiological parameter, and
wherein the IMD, the EMD, or the IMD and the EMD comprise a prescription component configured to:
select a diagnostic model from among a plurality of candidate diagnostic models; and
generate the study prescription based on the selected diagnostic model.

18. The system of claim 17, wherein the communication scheme that is configured based on the impact on the longevity of the at least one component of the IMD further corresponds to an amount of power consumption associated with information transmission from the IMD to the EMD.

19. The system of claim 17, wherein the impact on the longevity of the at least one component of the IMD corresponds to an amount of power consumption associated with operating the sensing component to obtain the values of the first physiological parameter.

* * * * *